(12) United States Patent
Barboza et al.

(10) Patent No.: US 8,425,930 B2
(45) Date of Patent: Apr. 23, 2013

(54) PREBIOTIC OLIGOSACCHARIDES

(75) Inventors: Mariana Barboza, Davis, CA (US); J. Bruce German, Davis, CA (US); Carlito Lebrilla, Davis, CA (US); David Mills, Davis, CA (US); Samara Freeman, Dublin (IE); William Robert King, Walnut Creek, CA (US)

(73) Assignees: The Regents of the University of California, Oakland, CA (US); DSM Food Specialties USA Inc., Parsippany, NY (US)

( * ) Notice: Subject to any disclaimer, the term of this patent is extended or adjusted under 35 U.S.C. 154(b) by 50 days.

(21) Appl. No.: 12/722,813

(22) Filed: Mar. 12, 2010

(65) Prior Publication Data

US 2010/0254949 A1 Oct. 7, 2010

Related U.S. Application Data

(60) Provisional application No. 61/160,088, filed on Mar. 13, 2009.

(51) Int. Cl.
*A61K 47/00* (2006.01)
*A01N 63/00* (2006.01)

(52) U.S. Cl.
USPC ......................... 424/439; 424/93.4

(58) Field of Classification Search .................. None
See application file for complete search history.

(56) References Cited

U.S. PATENT DOCUMENTS

| | | | |
|---|---|---|---|
| 6,576,251 B1 | 6/2003 | Stahl et al. | |
| 7,794,746 B2 * | 9/2010 | Gibson et al. | 424/439 |
| 2006/0165670 A1 | 7/2006 | Beer et al. | |
| 2007/0141678 A1 | 6/2007 | Green et al. | |
| 2010/0069322 A1 * | 3/2010 | Sinclair et al. | 514/54 |

FOREIGN PATENT DOCUMENTS

| | | |
|---|---|---|
| EP | 1887017 A1 | 2/2008 |
| WO | WO 2005/003329 A1 | 1/2005 |

OTHER PUBLICATIONS

Hopkins et al. Journal of Applied Microbiology. 1998, 85, pp. 381-386.*
Matsumoto et al. In: "Oligosaccharides: production, properties and applications". T.Nakakuri, Editor. 1995. Gordon and Breach Science Publishers: Shizuoka, Japan. Chapter 5, pp. 90-107.*
SCD Web Library "SCD Research, Fructooligosaccharides"; http://www.scdiet.org/6research/fos.html; webpage dated 2000 and retrieved on Aug. 30, 2012, pp. 1 and 2.*
Barboza, Mariana et al.; "Structural analysis of the N-glycans of the major cysteine proteinase of *Trypanosome cruzi*"; 2005, *FEBS Journal*, vol. 272, pp. 3803-3815.
Barboza, Mariana et al.; "Glycoprofiling Bifidobacterial Consumption of Galacto-Oligosaccharides by Mass Spectrometry Reveals Strain-Specific, Preferential Consumption of Glycans"; 2009, *Applied and Environmental Microbiology*, vol. 75, No. 23, pp. 7319-7325.
Bruckner, Reinhold et al.; "Carbon catabolite repression in bacteria: choice of the carbon source and autoregulatory limitation of sugar utilization"; 2002, *FEMS Microbiology Letters*, vol. 209, pp. 141-148.
Depeint, Flore et al.; "Prebiotic evaluation of a novel galactooligosaccharide mixture produced by the enzymatic activity of *Bifidobacterium bifidum* NCIMB 41171, in healthy humans: a randomized, double-blind, crossover, placebo-controlled intervention study"; 2008, Am. *J. Clin. Nutr.*, vol. 87, pp. 785-791.
MacFarlane, G.T. et al.; "Bacterial metabolism and health-related effects of galacto-oligosaccharides and other prebiotics"; 2007, *Journal of Applied Microbiology*, vol. 104, pp. 305-344.
Perez-Conesa, Dario et al.; "Fermentation Capabilities of Bifidobacteria Using Nondigestible Oligosaccharides, and Their Viability as Probiotics in Commercial Powder Infant Formula"; 2005, *Journal of Food Science*, vol. 70, No. 6, pp. 279-285.
Perez-Conesa, Dario et al.; "Fecal Microbiota Changes with the Consumption of Follow-up Formulas Containing *Bifidobacterium* spp. and/or Galactooligosaccharides by Rats and a Follow-up Infant Formula Containing *Bifidobacterium* spp. by Human Infants"; 2006, *Journal of Food Science*, vol. 71, No. 1, pp. 7-13.
Rabiu, Bodun A. et al.; "Synthesis and Fermentation Properties of Novel Galacto-Oligosaccharides by β-Galactosidases from *Bifidobacterium* Species"; 2001, *Applied and Environmental Microbiology*, vol. 67, No. 6, pp. 2526-2530.
Saier, M.H., Jr.; "Regulation of Carbon Metabolism in Bacteria"; 1996, *Res. Microbiol.*, vol. 147, pp. 439-587.
Saka, Tomoyuki et al.; "Recent progress on research and applications of non-digestible galacto-oligosaccharides"; 1999, *International Dairy Journal*, vol. 9, pp. 69-80.
Van Laere, Katrien M.J. et al.; "Characterization of a Novel β-Galactosidase from *Bifidobacterium adolescentis* DSM 20083 Active towards Transgalactooligosaccharides"; 2000, *Applied and Environmental Microbiology*, vol. 66, No. 4, pp. 1379-1384.
Vernazza, Claire L. et al.; "Carbohydrate preference, acid tolerance and bile tolerance in five strains of *Bifidobacterium*"; 2006, *Journal of Applied Microbiology*, vol. 100, pp. 846-853.
Kanamori et al.; "Combination therapy with *Bifidobacterium breve, Lactobaciffis casei*, and galactooligosaccharides dramatically improved the intestinal function in a girl with short bowel syndrome: a novel synbiotics therapy for intestinal failure"; *Digestive Diseases and Sciences*; 46(9):2010-2016 (Sep. 2001).
Tzortzis et al., "Synthesis of prebiotic galactooligosaccharides using whole cells of a novel strain, *Bifidobacterium bififdum* NCIMB 41171"; *Appl. Microbiol. Biotechnol.*; 68:412-416 (2005).

* cited by examiner

*Primary Examiner* — Vera Afremova
(74) *Attorney, Agent, or Firm* — Kilpatrick Townsend & Stockton LLP

(57) ABSTRACT

The present invention provides galacto-oligosaccharide compositions that preferentially stimulate growth of specific *Bifidobacterium* species and subspecies.

19 Claims, 10 Drawing Sheets

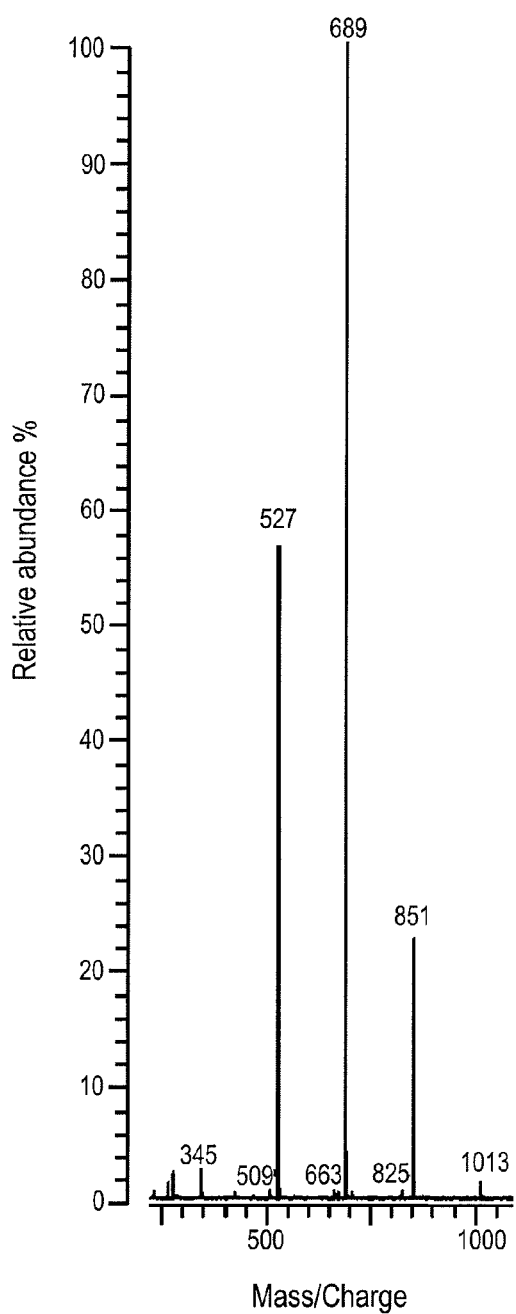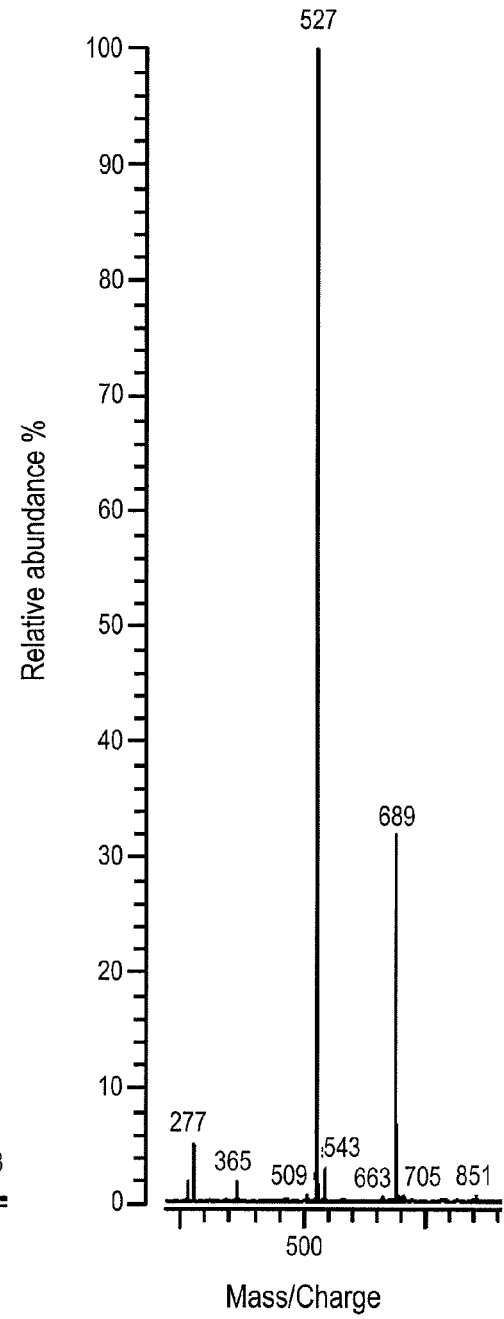
FIG. 2D  FIG. 2E

Positive MALDI-FTICR spectra of pGOS
with selected DP used in bifidobacterial fermentation experiments.

PREBIOTIC OLIGOSACCHARIDES

CROSS-REFERENCE TO RELATED PATENT APPLICATIONS

The present patent application claims benefit of priority to U.S. Provisional Patent Application No. 61/160,088, filed Mar. 13, 2009, which is incorporated by reference for all purposes.

BACKGROUND OF THE INVENTION

Galacto-oligosaccharides (GOS) are non-digestible carbohydrates and versatile food ingredients that possess prebiotic properties (Angus, F., Smart, S. and Shortt, C. 2005. In *Probiotic Dairy Products* ed. Tamine, A. pp. 120-137. Oxford: Blackwell Publishing). In addition, many other health benefits have been reported for these oligosaccharides including: improvement of defecation, stimulation of mineral absorption, elimination of ammonium, colon cancer prevention, as well as protection against certain pathogenic bacteria infections (Hopkins, M. J. and Macfarlane, G. T. 2003 *Appl Environ Microbiol* 69, 1920-1927; Shoaf, K., G. L. Mulvey, G. D. Armstrong, and R. W. Hutkins. 2006 *Infect Immun* 74:6920-8; Macfarlane, G. T., Steed H., Macfarlane S. 2008 *Journal of Applied Microbiology* 104, 305-44).

The human gastrointestinal tract (GIT) hosts a large bacterial population of 500-1000 different phylotypes that reside in the colon (Ninonuevo, M. R., et al. 2007 *Anal Biochem* 361,15-23). Among them, Bifidobacterial species are the predominant microbial in the infant GIT, exerting beneficial effects to their host such us immuno-stimulation, human pathogen inhibition, vitamin production, and anticarcinogenic activity, among others (Harmsen, H. J., et al. 2000 *J Pediatr Gastroenterol Nutr* 30:61-7; Casci, T., et al. 2007 Human Gut microflora in Health and Disease: Focus on Prebiotics. In *Functional food and Biotechnology*. Ed Taylor and Francis. pp 401-434). Due to these beneficial health effects, *Bifidobacteria* are considered probiotics and have being increasingly used in functional foods and pharmaceutical products (Stanton, C., et al. 2003. Challenges facing development of probiotics-containing functional foods. In *Handbook Fermented Functional Foods, Functional Foods and Nutraceutical Series*. CC Press, Boca Raton, Fla. pp 27-58).

The physicochemical characteristics of GOS have enabled them to be incorporated as prebiotic food ingredients in a variety of designed foods (Sako, T., et al. 1999 *Int Dairy J* 9, 69-80). GOS are of particular interest in confectionary acidic beverage and fermented milk foimulations as they possess increased thermal stability in acidic environments compared to FOS (Watanuki, M., et al. 1996 *Ann Report Yakult Central Inst Microbiol Res* 16, 1-12). Thus, in the past decade, GOS have also had an increasing application in human food products, including dairy products, sugar replacements and other diet supplements as well as infant formula (Macfarlane, G. T., Steed H., Macfarlane S. 2008 *Journal of Applied Microbiology* 104, 305-44).

Galacto-oligosaccharides are naturally occurring in human milk, however, commercial GOS preparations are produced by enzymatic treatment of lactose with β-galactosidases from different sources such as fungi, yeast and/or bacteria, yielding a mixture of oligomers with varied chain lengths (Angus, F., supra). Thus, the basic structure of GOS includes a lactose core at the reducing end which is elongated typically with up to six galactose residues. GOS structural diversity dependents on the enzyme used in the trans-galactosylation reaction, and the experimental conditions such as pH and temperature (Dumortier, V., et al. 1990. *Carbohydr Res* 201:115-23.).

Despite the amount of research claiming GOS bifidogenic effect, the vast majority of studies used commercially available preparations of GOS, containing high concentrations of monosaccharide (i.e. galactose and glucose) and the disaccharide lactose, all remaining reagents of the trans-galactosylation reaction. Notably, in the majority of reported cases, monosaccharides are the preferred substrates for microorganism when available in a mixed carbon source (Saier, M. H. Jr. 1996. *Res. Microbiol,* 147, 439-587; Bruckner, R. and Titgemeyer, F. 2002 *FEMS Microbiology Letters* 209, 141-48).

BRIEF SUMMARY OF THE INVENTION

The present invention provides compositions for stimulating growth of particular Bifidobateria. In some embodiments, the compositions comprise galacto-oligosaccharides, wherein at least 45% of the galacto-oligosaccharides by weight are tetra or penta galacto-oligosaccharides or wherein at least 25% of the galacto-oligosaccharides by weight are tetra galacto-oligosaccharides. In some embodiments, the compositions comprise galacto-oligosaccharides, wherein at least 30%, 40%, 50%, 60%, 75%, or 80% of the galacto-oligosaccharides by weight are tetra or penta galacto-oligosaccharides.

In some embodiments, the composition has less than 20% by weight of dimeric galacto-oligosaccharides based on weight of the total oligosaccharides. In some embodiments, the composition has less than 10% by weight of dimeric galacto-oligosaccharides based on weight of the total oligosaccharides.

In some embodiments, the composition has less than 5% by weight of monomeric sugars based on total sugar and oligosaccharide solids.

In some embodiments, the composition has less than 5% by weight of lactose, based on weight of the total oligosaccharides.

In some embodiments, the composition comprises a lactase enzyme (e.g., an encapsulated lactase that is degraded when ingested).

In some embodiments, the composition has less than 20% (e.g., less than 10%) by weight of dimeric galacto-oligosaccharides, and/or less than 5% by weight of monomeric galacto-oligosaccharides and/or less than 5% lactose.

In some embodiments, the composition is a food product or dietary supplement product.

In some embodiments, the food product is selected from the group consisting of an infant formula, a follow-on formula, and a toddler beverage.

In some embodiments, less than 10% of the galacto-oligosaccharides by weight have a degree of polymerization of 6 or greater.

In some embodiments, less than 10% of the galacto-oligosaccharides by weight are trimeric galacto-oligosaccharides.

In some embodiments, more than 30% of the galacto-oligosaccharides by weight are trimeric galacto-oligosaccharides.

In some embodiments, the compositions are prepared by a method comprising the step of treating a mixed galacto-oligosaccharide solution (GOS) to reduce monomeric, dimeric and/or trimeric sugars. In some embodiments, the monomeric, dimeric and/or trimeric sugars are removed by size exclusion or enzymatically, or by selective microbial consumption of particular sugars or oligosaccharides.

In some embodiments, the composition further comprises *Bifidobacterium breve* or *Bifidobacterium longum* bv. *infantis*.

The present invention also provides methods for stimulating beneficial *Bifidobacterium* microflora in an animal. In some embodiments, the method comprises administering a sufficient amount of the compositions described above or elsewhere herein to the animal to stimulate colonization of the gut of the animal by at least one beneficial *Bifidobacterium* strain.

In some embodiments, the strain is a strain of *Bifidobacterium breve* or *Bifidobacterium longum* bv. *infantis*.

In some embodiments, the animal is a human. In some embodiments, the animal is a non-human mammal.

In some embodiments, the human is less than 5 years old. In some embodiments, the human is over 50 years old. In some embodiments, the human has a condition selected from the group consisting of inflammatory bowel syndrome, constipation, diarrhea, colitis, Crohn's disease, colon cancer, functional bowel disorder, irritable bowel syndrome, and excess sulfate reducing bacteria.

Other aspects of the invention will be evident from the remaining text.

DEFINITIONS

The "degree of polymerization" or "DP" of a galacto-oligosaccharide refers to the total number of sugar monomer units that are part of a particular oligosaccharide. For example, a tetra galacto-oligosaccharide has a DP of 4, having 3 galactose moieties and one glucose moiety.

The term "*Bifidobacteria*" and its synonyms refer to a genus of anaerobic bacteria having beneficial properties for humans. *Bifidobacteria* is one of the major strains of bacteria that make up the gut flora, the bacteria that reside in the gastrointestinal tract and have health benefits for their hosts. See, e.g., Guarner F and Malagelada J R. *Lancet* (2003) 361, 512-519, for a further description of *Bifidobacteria* in the normal gut flora.

A "prebiotic" or "prebiotic nutrient" is generally a non-digestible food ingredient that beneficially affects a host when ingested by selectively stimulating the growth and/or the activity of one or a limited number of bacteria in the gastrointestinal tract. As used herein, the term "prebiotic" refers to the above described non-digestible food ingredients in their non-naturally occurring states, e.g., after purification, chemical or enzymatic synthesis as opposed to, for instance, in whole human milk.

A "probiotic" refers to live microorganisms that when administered in adequate amounts confer a health benefit on the host.

DETAILED DESCRIPTION OF THE INVENTION

I. Introduction

Figure 1:
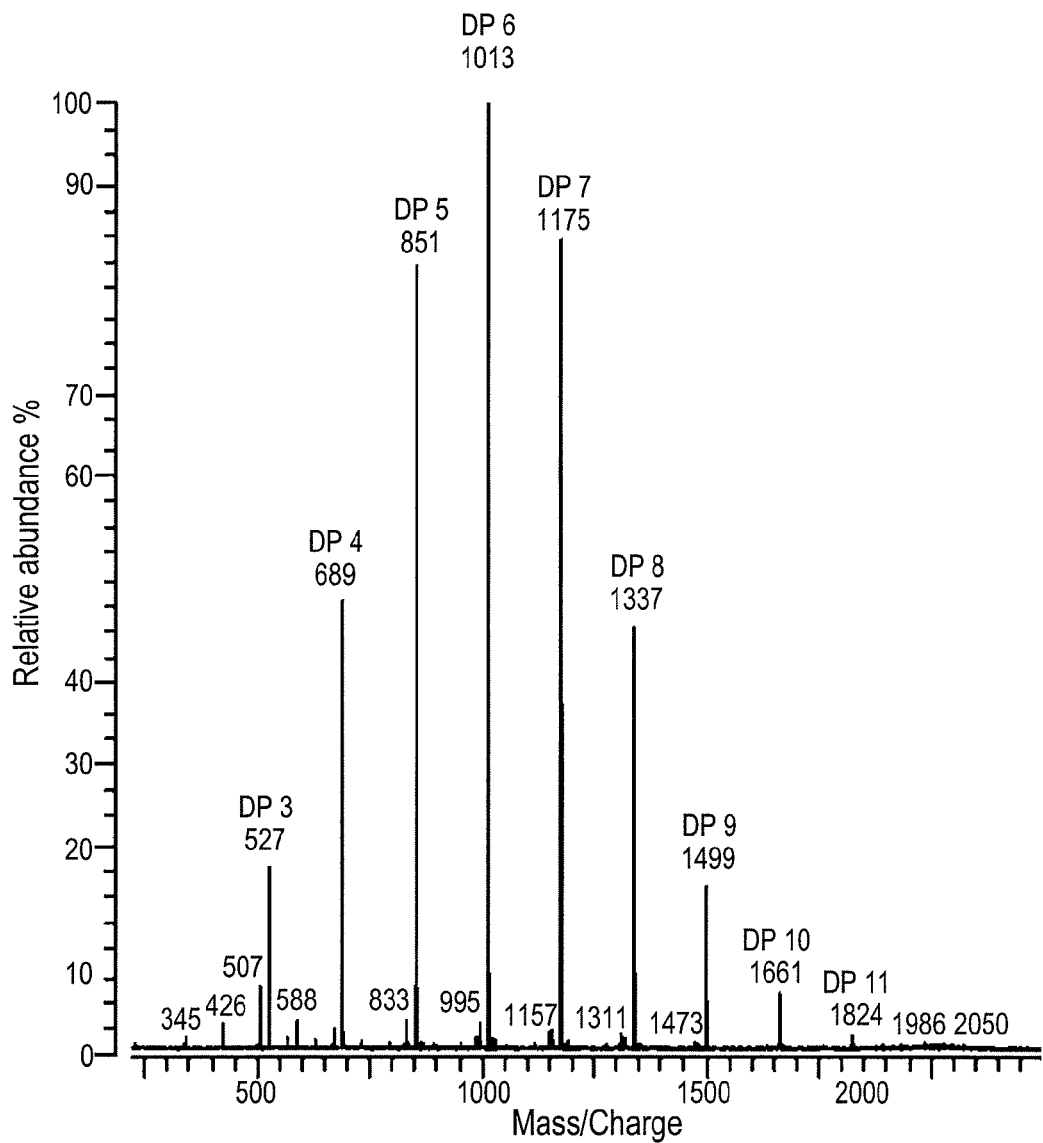
FIG. 1. Positive MALDI-FTICR ion spectra of syrup GOS. Major peaks correspond to sodium coordinated ions showing the degree of polymerization of GOS. Minor signals observed at 18 mass units less could correspond to B-type fragments.

Galacto-oligosaccharides are carbohydrates that possess prebiotic properties and that are non-digestible by humans. The present invention is based in part on the discovery that particular *Bifidobacterium* species or subspecies consume galacto-oligosaccharide polymers having a specific degree of polymerization (DP) but do not significantly consume other DPs. In view of these results, the invention provides for galacto-oligosaccharide compositions specifically designed to preferentially stimulate growth of specific *Bifidobacterium* species or subspecies in humans or other animals relative to other enteric bacteria.

II. Galacto-oligosaccharide Compositions

The galacto-oligosaccharide compositions of the invention can comprise the galacto-oligosaccharides themselves as well as optionally other components as desired for a particular use. The galacto-oligosaccharide compositions are synthetic (e.g., are generated by purified enzymatic reactions or as part of a human-directed fermentation process), and in some embodiments are purified. As discussed in more detail below, the galacto-oligosaccharides can be combined with various ingredients to manufacture food stuffs and food supplements including, for example, infant formulas. The compositions can further optionally comprise beneficial bacteria, notably particular *Bifidobacterium* species or subspecies.

A. Galacto-oligosaccharides

Galacto-oligosaccharides refer to straight or branched polymers of galactose. Generally, galacto-oligosaccharides are made up solely of galactose units with the exception that the terminal sugar is glucose. Galacto-oligosaccharides can therefore be represented by the formula Gal-(Gal)$_n$-Glc, where Gal is a galactose residue, Glc is a glucose residue, and n is an integer of zero or greater.

The present invention provides for GOS compositions that are enriched for particular DPs that can be used to preferentially stimulate growth of specific *Bifidobacteria*. For example, the following summarizes some of the findings of the inventors:

1. Infant-borne *Bifidobacteria* (e.g., *B. breve* and *B. longum* bv *infantis*) growth can be preferentially stimulated (e.g., relative to other enteric bacteria including other *Bifidobacteria*) using GOS that is enriched for DP 4-5 galacto-oligosaccharides.
2. Adult-borne *Bifidobacteria* (*B. longum* bv *longum*) growth can be preferentially stimulated using GOS that is enriched for DP 6-8 galacto-oligosaccharides.

3. *B. longum* bv. *infantis* and *B. adolescentis* species growth can be preferentially stimulated using GOS that is enriched for DP 3 galacto-oligosaccharides.

i. Galacto-oligosaccharides that Enrich *Bifidobacteria infantis* or *breve*

As noted above and in the Example, galacto-oligosaccharides of DP 4-5 are consumed by *Bifidobacteria* typically found in infants, e.g., *Bifidobacteria infantis* or *breve*.

Accordingly, in some embodiments, the compositions of the present invention comprise galacto-oligosaccharides, wherein at least 20%, 25%, 30%, 35%, 40%, 45%, or 50% of the galacto-oligosaccharides by weight are tetra galacto-oligosaccharides and/or optionally at least 20%, 25%, 30%, 35%, 40%, 45%, or 50% of the galacto-oligosaccharides by weight are penta galacto-oligosaccharides. All composition percentages as provided herein, unless indicated otherwise, are determined by mass spectrometry (e.g., MALDI-FTICR as described in the Examples). In some embodiments, the compositions of the present invention comprise galacto-oligosaccharides, wherein at least 30%, 40%, 50%, 60%, 70%, 80%, or 90% of the galacto-oligosaccharides by weight are DP4-5 galacto-oligosaccharides. These embodiments are useful, for example, for enriching for *Bifidobacteria infantis* or *breve*. In some embodiments, the compositions have less than 10% or less than 5% of monomeric sugars (e.g., galactose) and/or less than 10% or less than 5% of lactose and/or optionally less than 10% or less than 5% of dimeric galacto-oligosaccharides. In some embodiments, the compositions also have less than 10% or less than 5% of trimeric (DP3) galacto-oligosaccharides. As used herein, a percentage of a particular DP refers to the amount by weight of the particular DP relative to the weight of total sugars (including galactose monomers) in the composition.

Alternatively, in some embodiments, compositions are enriched for DP 3-6, i.e., including trimeric, galacto-oligosaccharides. In some embodiments, at least 30%, 40%, 50%, 60%, 70%, 80%, or 90% of the sugars in the composition are galacto-oligosaccharides having a DP of 3-6. Such embodiments will optionally have less than 10% or less than 5% of monomeric sugars (e.g., galactose) and optionally less than 10% or less than 5% of dimeric galacto-oligosaccharides.

Any of the compositions of the invention, including but not limited to infant or follow-on formula, can include supplements of lactose as well as other sugars or vitamins as well as other components, including but not limited to, *Bifidobacteria* species and subspecies as described herein.

Any of the above-described compositions can also be selected to have low or no galacto-oligosaccharides of DP 6 or above. Thus, in some embodiments, the compositions have less than 10% or less than 5% of DP 6+ galacto-oligosaccharides.

The present invention also provides for compositions comprising galacto-oligosaccharides wherein galacto-oligosaccharides having DP 4-5 are enriched (e.g., are at least 5%, 10%, 15%, 20%, 30%, 40% more than) compared to the amount by weight of DP 4-5 in a mixed galacto-oligosaccharide solution. "A mixed galacto-oligosaccharide solution" refers to a mix of galacto-oligosaccharides having different DPs, e.g., as is produced using a β-galactosidase in a transgalactosylation reaction (e.g., as described in Japanese Patent JP105109 or U.S. Pat. No. 4,957,860). Exemplary mixed galacto-oligosaccharide solutions include, e.g., Vivinal™ GOS (available from Friesland Foods Domo, The Netherlands). In some embodiments, the enriched compositions of the invention have less than 10% or less than 5% of sugar monomers (e.g., galactose) and optionally less than 10% or less than 5% of dimeric galacto-oligosaccharides. In some embodiments, the enriched compositions of the invention also have less than 10% or less than 5% of trimeric (DP3) galacto-oligosaccharides.

ii. Galacto-oligosaccharides that Enrich *Bifidobacteria longum*

As noted above and in the Example, galacto-oligosaccharides of DP 6-8 are consumed by *Bifidobacteria* typically found in adults, e.g., *Bifidobacteria longum*. Accordingly, in some embodiments, the compositions of the present invention comprise galacto-oligosaccharides, wherein at least 30%, 40%, 50%, 60%, 70%, 80%, or 90% of the galacto-oligosaccharides by weight are DP 6-8 galacto-oligosaccharides. In some embodiments, the compositions have less than 10% or less than 5% of monomeric sugars (e.g., galactose) and optionally less than 10% or less than 5% of dimeric galacto-oligosaccharides. In some embodiments, the compositions also have less than 10% or less than 5% of galacto-oligosaccharides with a DP of 3, 4, and/or 5. Any of the compositions of the invention can include supplements of lactose as well as other sugars or vitamins as other components, including but not limited to, *Bifidobacteria* species and subspecies as described herein.

The present invention also provides for compositions comprising galacto-oligosaccharides wherein galacto-oligosaccharides having DP 6-8 are enriched (e.g., are at least 5%, 10%, 15%, 20%, 30%, 40% more than) compared to the amount by weight of DP 6-8 in mixed galacto-oligosaccharide solutions, e.g., such as described above or as in Vivinal™ GOS. In some embodiments, the compositions have less than 10% or less than 5% of monomeric sugars (e.g., galactose) and optionally less than 10% or less than 5% of dimeric galacto-oligosaccharides. In some embodiments, the compositions also have less than 10% or less than 5% of DP 3, 4, 5, and/or 6 galacto-oligosaccharides.

iii. Additional Galacto-oligosaccharides that Enrich *B. longum* bv. *infantis* and *B. adolescentis* Species As noted above and in the Example, galacto-oligosaccharides of DP 3 are consumed by *B. longum* bv. *infantis* and *B. adolescentis* species. Accordingly, in some embodiments, the compositions of the present invention comprise galacto-oligosaccharides, wherein at least 30%, 40%, 50%, 60%, 70%, 80%, or 90% of the galacto-oligosaccharides by weight are DP 3 galacto-oligosaccharides. In some embodiments, the compositions have less than 10% or less than 5% of sugar monomers (e.g., galactose) and optionally less than 10% or less than 5% of dimeric galacto-oligosaccharides. In some embodiments, the compositions also have less than 10% or less than 5% of DP 4 or greater galacto-oligosaccharides. Any of the compositions of the invention can include supplements of lactose as well as other sugars or vitamins as other components, including but not limited to, *Bifidobacteria* species and subspecies as described herein.

The present invention also provides for compositions comprising galacto-oligosaccharides wherein galacto-oligosaccharides having DP 3 are enriched (e.g., are at least 5%, 10%, 15%, 20%, 30%, 40% more than) compared to the amount by weight of DP 3 in mixed galacto-oligosaccharide solutions such as described above or as in Vivinal™ GOS. In some embodiments, the compositions have less than 10% or less than 5% of monomeric sugars (e.g., galactose) and optionally less than 10% or less than 5% of dimeric galacto-oligosaccharides.

iv. Methods of Making the Galacto-oligosaccharide Compositions of the Invention In some embodiments, galacto-oligosaccharides are produced as mixtures (known in the art as "GOS") of oligosaccharides having different degrees of polymerization (i.e., "DP" or the number of monomeric units in the polymer). For example, in some embodiments, galacto-oligosaccharides are synthesized enzymatically from monomeric or dimeric sugars. Galacto-oligosaccharides can be produced, for example, from lactose syrup using the transgalactosylase activity of the enzyme β-galactosidase (Crittenden, (1999) *Probiotics: A Critical Review*. Tannock, G.(ed) Horizon Scientific Press, Wymondham, pp. 141-156). Other general GOS production methods include, e.g., production of galacto-oligosaccharide by treating lactose with beta-galactosidase derived from *Bacillus circulans* (see, e.g., Japanese Patent JP105109 and production by the reaction between lactose and beta-galactosidase from *Aspergillus oryzae* (see, e.g., U.S. Pat. No. 4,957,860). See also, e.g., Ito et al., Microbial *Ecology in Health and Disease*, 3, 285-292 (1990). A related method utilizes the β-galactosidase of *Bifidobacterium bifidum* NCIMB 41171 to synthesize prebiotic galacto-oligosaccharides (see, Tzortzis et al., Appl. Micro. and Biotech. (2005), 68:412-416). Commercial GOS products are also available that generally and generally include a wide spectrum of different-sized galacto-oligosaccharides.

Thus, to generate the specific purified galactooligosaccharides of the present invention (e.g., lacking, or being enriched for, sugars of a particular size), in some embodiments, the compositions of the present invention can be generated by obtaining a GOS mixture containing a variety of different-sized galacto-oligosaccharides and then reducing the proportion of galacto-oligosaccharides having a DP that is not desired. For example, in some embodiments, galacto-oligosaccharides having a DP of 1, 1-2, 1-3, etc. can be reduced, for example, by size exclusion technology, enzymatic degradation, selective microbial consumption or a combination thereof. An example of selective microbial consumption is the use of *Kluyveromyces lactis* or other *Kluyveromyces* species to selectively consume DP2 sugars, for example.

Alternatively, or optionally in addition, enzymatic methods can be used to synthesize the galacto-oligosaccharides of the present invention. In general, any oligosaccharide biosynthetic enzyme or catabolic enzyme (with the reaction running in reverse) that converts a substrate into any of the target DP of the galacto-oligosaccharide(or their intermediates) may be used in the practice of this invention. For example, prebiotic galacto-oligosaccharides have been synthesized from lactose using the β-galactosidase from *L. reuteri* (see, Splechtna et al., *J. Agricultural and Food Chemistry* (2006), 54: 4999-5006). The reaction employed is known as transgalactosylation, whereby the enzyme β-galactosidase hydrolyzes lactose, and, instead of transferring the galactose unit to the hydroxyl group of water, the enzyme transfers galactose to another carbohydrate to result in oligosaccharides with a higher degree of polymerization (Vandamme and Soetaert, *FEMS Microbiol. Rev.* (1995), 16:163-186). The transgalactosylation reaction can proceed intermolecularly or intramolecularly. Intramolecular or direct galactosyl transfer to D-glucose yields regioisomers of lactose. Through intermolecular transgalactosylation di-, tri-, and tetra saccharides and eventually higher oligosaccharides specific to *Bifidobacteria* can produced and subsequently purified as desired.

Optionally, the galacto-oligosaccharide compositions of the invention can be made by contacting a first solution comprising lactose with a lactase (e.g., a transferase type of lactase) to convert at least part of the lactose into oligosaccharides, resulting in a second solution of oligosaccharides and lactose, contacting the second solution with a lactase (e.g., a hydrolytic type of lactase), and optionally separating monomeric or other sugars (e.g., lactose, dimeric sugars) from the solution. In some embodiments, the galacto-oligosaccharide composition will comprise lactose and the composition is formulated to comprise one or more lactase (e.g., an encapsulated lactase that is degraded following ingestion, thereby allowing for relase of the lactase and digestion of the lactose).

In some embodiments, the process for the preparation of the claimed galactose-oligosaccharides compositions can comprise the following steps:

1. Incubation of a lactose containing solution under proper conditions with a β-galactosidase preparation. The β-galactosidase preparation can be characterized by containing (optionally only) enzymes that have high transgalactosidase activity (transferase type lactases such as provided by the β-galactosidases derived from *Aspergillus oryzae*, *Bacillus circulans*, *Streptococcus thermophilus* and *Lactobacillus bulgaricus*). The β-galactosidase preparation may also consist of a mixture of such β-galactosidases. Reaction conditions can be optimized for the β-galactosidase enzyme preparation. In some embodiments, the reaction is allowed to proceed until no significant additional formation of oligosaccharides is observed.

2. Addition of a β-galactosidase preparation that shows high hydrolytic activity (a hydrolytic type lactase) such as lactases derived from *Kluyveromyces lactis*, *Kluyveromyces fragilis* or *Aspergilus niger*. Reaction conditions can be optimized for the β-galactosidase enzyme preparation. In some embodiments, the reaction is allowed to proceed until lactose levels are at least lower than 5% of total sugars.

The reaction mixture can then optionally be further processed as desired, including steps like heat-inactivation of the enzymes, ultra-filtration to remove enzymes and nano-filtration to reduce mono sugar concentrations. The final preparations may be stored as a stabilized liquid or alternatively it may be dried. Methods for stabilization and drying are known to the expert in the art. In some embodiments, the second step in the process does not lead to a reduction in concentration of galacto-oligosaccharides but instead leads to an increase of yield of these components.

A detailed process for the preparation of improved oligosaccharide compositions is provided below: An aqueous solution containing lactose (e.g., 50-400 g/L) is prepared. At this stage, cofactors like metal ions (e.g. $Mg^{2+}$, $Mn^{2+}$, $Zn^{2+}$, $Na^+$, $K^+$, etc) may be added to improve enzyme stability in the process. The production method consists of three main steps. In step 1, most of the galacto-oligosaccharides are produced. In step 2, lactose levels are reduced below 5% of total sugars and oligosaccharide production is further increased. In step 3, monomeric sugars are optionally removed from the oligosaccharide composition and the remaining solution is further processed into a stabilized liquid; alternatively, it may be dried using methods known to the expert in the field.

In step 1 of the process, the solution is treated with a transferase type β-galactosidase. To this purpose transferase type acid lactases may be used, and the lactose containing solution is in this case adjusted preferably to a pH between 2.5 and 5.5, using hydrochloric acid, acetic acid or any other suitable acid. Alternatively, buffer solutions such as 50 mM Na-acetate buffer or any other suitable buffer may be used to set the pH. After pH adjustment, acid lactase derived from Aspergillus oryzae (Tolerase, DSM, The Netherlands), is added to an end concentration of preferably 1,000-10,000 ALU per liter. Other suitable examples include but are not limited to a β-galactosidase derived from *Bacillus circulans* or *Lactobacillus reuteri*. "ALU" refers to Acid Lactase Units, which is defined as the amount of enzyme required to release one micromole of o-nitrophenol from o-nitrophenyl-β-D-galactopyranoside in one minute under the defined conditions (pH=4.5, T=37.00 C).

Instead of Tolerase, any suitable other transferase type acid lactase may be added, or a combination of suitable transferase type acid lactases may be used. The reaction mixture can optionally be heated to any suitable temperature preferably between 30° C. and 60° C. The optimal temperature depends on the specific lactase or combination of lactases used. In some embodiments, the reaction mixture is kept at this optimal temperature for, e.g., 2-48 hours, but alternatively temperature gradients may be applied during this period. Optionally, a transferase type acid lactase may be added to the reaction mixture during this period to improve formation of oligosaccharides. A transferase type neutral lactase, like the lactase from *Bacillus circulans*, may also be used in the first step of the process instead of an acid lactase or combination of acid lactases. In that case, the pH of the concentrated lactose solution is adjusted to any suitable pH between preferably pH 5.0 and 8.0 using HCl, acetic acid, or any suitable acid, NaOH, ammonium hydroxide or any suitable base or buffer, after that the reaction is allowed to proceed as described for the acid lactases. The use of a combination of transferase type neutral lactases or the addition of a neutral lactase during step 1 is optional. After this first step, the reaction mixture is optionally cooled to any suitable temperature, and when required the pH is adjusted to the pH that is most suitable for step 2 of the process.

In step 2 of the process, a hydrolytic type lactase is used. For example, a hydrolytic type neutral lactase such as derived from *Kluyveromyces lactis* (Maxilact, DSM, The Netherlands) is used at a concentration preferably between 1,000 and 10,000 NLU per liter. "NLU" refers to Neutral Lactase Units, which is defined as the amount of enzyme that will form 1.30 umol ortho-nitro-phenol from the synthetic substrate ortho-nitro-phenol-galacto-pyranoside under the test conditions (pH=6.5, T=37.00 C). Other suitable examples include, but are not limited to, a hydrolytic type neutral lactase derived from *Aspergillus niger* or *Streptococcus thermophilus*.

In some embodiments, the reaction is allowed to proceed for 2-48 hours, e.g., at temperatures between 10 and 60° C. Alternatively, temperature gradients may be used during the incubation. Reaction conditions are optimized for lactose hydrolysis. The reaction is allowed to proceed until lactose concentration is below 5% of total sugars. In step 2, combinations of hydrolytic type neutral lactases may be used. Hydrolytic type neutral lactases may be added during the incubation of step 2 to help to reduce lactose levels. A hydrolytic type acid lactase may also be used in step 2 instead of the hydrolytic type neutral lactase. In that case the pH of the solution is adjusted to any suitable pH, including but not limited to, between 2.5 and 5.5, using hydrochloric acid, acetic acid or any other suitable acid. Alternatively, buffers like 50 mM Na-acetate buffer or any other suitable buffer may be used to set the pH. Suitable lactases may be derived from e.g. *Aspergillus niger* and may be added to concentrations of preferably 1,000-10,000 ALU/L and the reaction is allowed to proceed, e.g., between 2-48 hours at temperatures between, e.g., 20 and 60° C. Instead of a single hydrolytic type acid lactase, combinations of hydrolytic type acid lactases may be used in this step. It is an option to add an additional lactase during the incubation in this second step. The reaction conditions are optimized to obtain lactose hydrolysis until final lactose concentration is below 5% of total sugars and without significant degrading of formed previously oligosaccharides. At the end of step 2, the temperature may be raised to inactivate enzymes.

In step 3, the solution containing galacto-oligosaccharides is optionally further processed to remove enzymes and mono sugars. Enzymes may be removed by ultra filtration; suitable filters are well known to the person skilled in the art. The resulting mono sugars (primarily glucose and galactose) may subsequently be removed by nanofltration. Suitable filters and filtration conditions are known to the person skilled in the art, and have been described in literature as described previously in this text. The resulting oligosaccharide composition is than essentially free from enzymes and monomeric sugars and can be further processed into a stabilized liquid or can be dried using methods known to the person skilled in the art to obtain e.g. a powder or granulate products.

The enzymes used in a method of the invention can be used either in the free form without restriction of movement in the reaction mixture or alternatively can be immobilized on a suitable carrier. Immobilization can be obtained by covalent coupling of the enzyme to a carrier substrate or by physical entrapment of the enzyme in e.g. a gel matrix. Methods to immobilize enzymes are known to the expert in the field; recent reviews have appeared on this topic (see e.g. Mateo et al 2007, *Enz. Micr. Technol.* 40, 1451-1463). Enzymes may also be cross-linked to form large aggregates that can easily be separated from the reaction mature by filtration (see for review e.g. Margolin et al, 2001, *Angew. Chem. Int. Ed.* 40, 2204-2222).

Alternatively, conventional chemical methods may be used for the de novo organic synthesis of or conversion of pre-existing oligosaccharides into the galacto-oligosaccharides having DPs of the present invention. See, e.g., March's Advanced Organic Chemistry: Reactions, Mechanisms, and Structure, 5th Edition.

B. Prebiotic and Probiotic Formulations

The galacto-oligosaccharides compositions of the present invention can be administered as a prebiotic formulation (i.e., without bacteria) or as a probiotic formulation (i.e., with desirable bacteria such as *bifidobacteria* as described herein). In general, any food or beverage that can be consumed by human infants or adults or animals may be used to make formulations containing the prebiotic and probiotic compositions of the present invention. Exemplary foods include those with a semi-liquid consistency to allow easy and uniform dispersal of the prebiotic and probiotic compositions of the invention. However, other consistencies (e.g., powders, liquids, etc.) can also be used without limitation. Accordingly, such food items include, without limitation, dairy-based products such as cheese, cottage cheese, yogurt, and ice cream. Processed fruits and vegetables, including those targeted for infants/toddlers, such as apple sauce or strained peas and carrots, are also suitable for use in combination with the galacto-oligosaccharides of the present invention. Both infant cereals such as rice- or oat-based cereals and adult cereals such as Musilix are also be suitable for use in combination with the galacto-oligosaccharides of the present invention. In addition to foods targeted for human consumption, animal feeds may also be supplemented with the prebiotic and probiotic compositions of the invention.

Alternatively, the prebiotic and probiotic compositions of the invention may be used to supplement a beverage. Examples of such beverages include, without limitation, infant formula, follow-on formula, toddler's beverage, milk, fermented milk, fruit juice, fruit-based drinks, and sports drinks. Many infant and toddler formulas are known in the art and are commercially available, including, for example, Carnation Good Start (Nestle Nutrition Division; Glendale, Calif.) and Nutrish A/B produced by Mayfield Dairy Farms (Athens, Tenn.). Other examples of infant or baby formula include those disclosed in U.S. Pat. No. 5,902,617. Other beneficial formulations of the compositions of the present invention include the supplementation of animal milks, such as cow's milk.

Alternatively, the prebiotic and probiotic compositions of the present invention can be formulated into pills or tablets or encapsulated in capsules, such as gelatin capsules. Tablet forms can optionally include, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The inventive prebiotic or probiotic formulations may also contain conventional food supplement fillers and extenders such as, for example, rice flour.

In some embodiments, the prebiotic or probiotic composition will further comprise a non-human protein, non-human lipid, non-human carbohydrate, or other non-human component. For example, in some embodiments, the compositions of the invention comprise a bovine (or other non-human) milk protein, a soy protein, a rice protein, betalactoglobulin, whey, soybean oil or starch.

The dosages of the prebiotic and probiotic compositions of the present invention will be varied depending upon the requirements of the individual and will take into account factors such as age (infant versus adult), weight, and reasons for loss of beneficial gut bacteria (e.g., antibiotic therapy, chemotherapy, disease, or age). The amount administered to an individual, in the context of the present invention should be sufficient to establish colonization of the gut with beneficial bacteria over time. The size of the dose also will be determined by the existence, nature, and extent of any adverse side-effects that may accompany the administration of a prebiotic or probiotic composition of the present invention. In some embodiments, the dosage range will be effective as a food supplement and for reestablishing beneficial bacteria in the intestinal tract. In some embodiments, the dosage of a galacto-oligosaccharide composition of the present invention ranges from about 1 micrograms/L to about 25 grams/L of galacto-oligosaccharides. In some embodiments, the dosage of a galacto-oligosaccharide composition of the present invention is about 100 micrograms/L to about 15 grams/L of galacto-oligosaccharides. In some embodiments, the dosage of a galacto-oligosaccharide composition of the present invention is 1 gram/L to 10 grams/L of galacto-oligosaccharides. Exemplary *Bifidobacteria* dosages include, but are not limited to, $10^4$ to $10^{12}$ colony forming units (CFU) per dose. A further advantageous range is $10^6$ to $10^{10}$ CFU.

The prebiotic or probiotic formulations of the invention can be administered to any individual in need thereof. In some embodiments, the individual is an infant or toddler. For example, in some embodiments, the individual is less than, e.g., 3 months, 6 moths, 9 months, one year, two years or three years old. In some embodiments, the individual is an adult. For example, in some embodiments, the individual is over 50, 55, 60, 65, 70, or 75 years old. In some embodiments, the individual is immuno-deficient (e.g., the individual has AIDS or is taking chemotherapy).

Exemplary *Bifidobacteria* that can be included in the probiotic compositions of the invention include, but are not limited to, *B. longum* bv *infantis*, *B. longum* bv *longum*, *B. breve*, and *B. adolescentis*. The *Bifidobacterium* used will depend in part on the target consumer.

For example, in some embodiments, *B. longum* bv *infantis* is administered with the galacto-oligosaccharide compositions of the invention to an infant or young child (e.g., under 5 years old). In some embodiments, *B. longum* bv *infantis* is included in, or in conjunction with, an infant formula or follow-on formula. In some of these embodiments, the galacto-oligosaccharide compositions of the invention are enriched for DP 4-5 galacto-oligosaccharides, optionally having less than 5% by weight of dimeric and trimeric galacto-oligosaccharides. In some embodiments, the compositions are administered to an adult or an elderly person. In some embodiments, the person is at least 50, 60, 70, or 80 years old.

It will be appreciated that it may be advantageous for some applications to include other Bifidogenic factors in the formulations of the present invention. Such additional components may include, but are not limited to, fructoligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as lactose, xylooligosaccharides, soyoligosaccharides, lactulose/lactitol, among others. In some applications, other beneficial bacteria, such as *Lactobacillus*, can be included in the formulations.

In some embodiments, the compositions of the invention are administered to a human or animal in need thereof. For example, in some embodiments, the compositions of the invention are administered to a person or animal having at least one condition selected from the group consisting of inflammatory bowel syndrome, constipation, diarrhea, colitis, Crohn's disease, colon cancer, functional bowel disorder (FBD), irritable bowel syndrome (IBS), excess sulfate reducing bacteria, inflammatory bowel disease (IBD), and ulcerative colitis. Irritable bowel syndrome (IBS) is characterized by abdominal pain and discomfort, bloating, and altered bowel function, constipation and/or diarrhea. There are three groups of IBS: Constipation predominant IBS (C-IBS), Alternating IBS (A-IBS) and Diarrhea predominant IBS (D-IBS). The compositions of the invention are useful, e.g., for repressing or prolonging the remission periods on Ulcerative patients. The compositions of the invention can be administered to treat or prevent any form of Functional Bowel Disorder (FBD), and in particular Irritable Bowel Syndrome (IBS), such as Constipation predominant IBS (C-IBS), Alternating IBS (A-IBS) and Diarrhea predominant IBS (D-ESS); functional constipation and functional diarrhea. FBD is a general term for a range of gastrointestinal disorders which are chronic or semi-chronic and which are associated with bowel pain, disturbed bowel function and social disruption.

In another embodiment of the invention, the compositions of the invention are administered to those in need stimulation of the immune system and/or for promotion of resistance to bacterial or yeast infections, e.g., Candidiasis or diseases induced by sulfate reducing bacteria.

EXAMPLES

The following examples are offered to illustrate, but not to limit the claimed invention. Those of skill in the art will readily recognize a variety of noncritical parameters that could be changed or modified to yield essentially similar results.

Example 1

We have previously developed analytical methods employing high mass accuracy and high resolution Fourier Transform Ion Cyclotron (FTICR) mass spectrometry to characterize bacterial consumption of human milk oligosaccharides (HMOs) and fructo-oligosaccharides (FOS) (Ninonuevo, M. R. et al., *Anal Biochem,* 361:15-23 (2007); LoCascio, R. G. et al., *J Agric Food Chem,* 55:8914-9 (2007); Seipert, R. R. et al., *Anal Chem,* 80:159-65 (2008)). MALDI-FTICR was shown to be a sensitive and robust analytical method with high-performance capabilities, allowing rapid and unambiguous assignments of oligosaccharide signals.

In the present study, the oligosaccharide composition in GOS syrup preparations was investigated by MALDI-FTICR. Moreover, disaccharide- and monosaccharide-free fractions of GOS (termed pGOS) were prepared by size-exclusion chromatography and used in bacterial fermentation experiments. Four major bifidobacterial species, *Bifidobacterium adolescentis, B. breve, B. longum* subsp. *Infantis,* and *B. longum* subsp. *longum,* present in infants and adult intestinal microbiota were assayed and pGOS consumption profiles were obtained by MALDI-FTICR mass spectrometry.

Material and Methods

Bacterial strains. *Bifidobacterium adolescentis* ATCC 15703, *B. breve* ATCC 15700 and *B. longum* subsp. *infantis* ATCC 15697 were obtained from the American type Culture Collection (Manassas, Va.). *B. longum* subsp. *longum* DJO10A was a gift from D. O'Sullivan, University of Minnesota.

Galacto-oligosaccharides purification. Galacto-oligosaccharides purification.

The purified GOS mixture (termed pGOS) was obtained by purification from Vivinal™ GOS (Domo Friesland Food, location?). Sugars with degree of polymerization (DP) less than 2 (including lactose, glucose and galactose) were removed by Bio-Gel P-2 gel size-exclusion chromatography (110×2.6 cm with a 200/400 mesh, Bio-Rad) at room temperature using water as the eluent and a flow rate was 0.16 ml/min. One mL fractions were collected and analyzed by MALDI-FTICR MS. Fractions containing oligosaccharides with a DP>=3 were pooled for bacterial fermentation experiments. Thin layer chromatography was performed to confirm lactose-free pGOS obtained in a solvent mixture of acetonitrile/water (8:2 v/v). The plate was developed twice at room temperature, dried and visualized using 0.3% (w/v) N-(1-naphthyl)-ethylenediamine and 5% (v/v) $H_2SO_4$ in methanol, followed by heating at 110° C. for 10 min (Lee H Y, M. J. et al., *Journal of Molecular Catalysis B: Enzymatic,* 26:293-305 (2003)).

Bacterial fermentations. *Bifidobacteria* cultures were initially propagated on a semi-synthetic MRS medium supplemented with 1% L-cysteine and 1.5% (w/v) lactose as a carbon source. Cultures were then inoculated at 1% into a modified MRS medium supplemented with 1% L-cysteine, containing 0.5, 1, 1.5 or 2% (w/v) of pGOS as a sole carbon source. Growth studies were carried out in a 96 well-plate (clear, non-treated, polysterene 96 well-plate from Nunc), containing 100 µl of media/well and each well was covered with 40 µl of mineral oil. Incubations were carried out at 37° C. and cell growth was measured by assessing optical density (OD) at 600 nm with an automated PowerWave microplate spectrophotometer (BioTek Instruments, Inc.), placed inside of an anaerobic chamber (Coy Laboratory Products, Grass Lake, Mich.). Each fermentation experiment was performed in triplicates, and controls consisted of inoculated medium lacking pGOS and un-inoculated medium containing pGOS.

pGOS purification after fermentation. After cell growth, the residual pGOS was recovered and purified from supernatant cultures. Samples (100 µl) were collected 72 hours post-inoculation, centrifuged at 4000×g for 10 min. The resulting supernatant, were transferred into new tubes, heated at 95° C. for 5 min, sterile-filtered with Millex-GV (0.22 µm, Millipore, Mass.), and stored at −80° C. Oligosaccharides were then purified from the supernatant using microcolumns containing 100 µL Dowex 50WX8 H⁺ form (Supelco, Bellefonte, Pa.) (bottom) and 100 µL of C18 resins (taken from disposable C18 cartridge (Waters, Milford, Mass.) (top). Resins were packed into empty columns (MicroBio-Spin columns, Bio-Rad, Hercules, Calif.) with nano-pure water. Supernatants samples were applied and pGOS was eluted with 0.3 mL water, dried down in vacuum and stored at −80° C. Samples were then reconstituted in deionized water to initial concentration before MS analyses.

MALDI-FTICR MS analysis. All mass analyses were carried out with a

ProMALDI-FT-ICR MS instrument with an external MALDI source, a 355 nm pulsed Nd:YAG laser, a hexapole accumulation cell, a quadrupole ion guide, and a 7.0-T superconducting magnet (Varian/IonSpec, Lake Forest, Calif.). Tandem MS was performed by IRMPD and a $CO_2$ laser (10.6 ím, 20-W maximum power, Parallax, Waltham, Mass.) was added to the instrument in order to provide IR photons for these experiments. DHB (0.4 M in acetonitrile:water (50% v/v)) and 0.10 mM NaCl, were used as matrix and dopant, respectively; samples were spotted onto a 100-well stainless steel sample plate (Applied Biosystems, Foster City, Calif.), according to the "thin layer" method. Samples were analyzed in the positive ion mode, with external accumulation of ions in the hexapole; ions were then transferred to the ICR cell via the ion guide for excitation and detection. In tandem, IRMPD experiments select precursor ions were isolated in the ICR cell and irradiated with photons for 500 ms.

Results

Figure 2A:
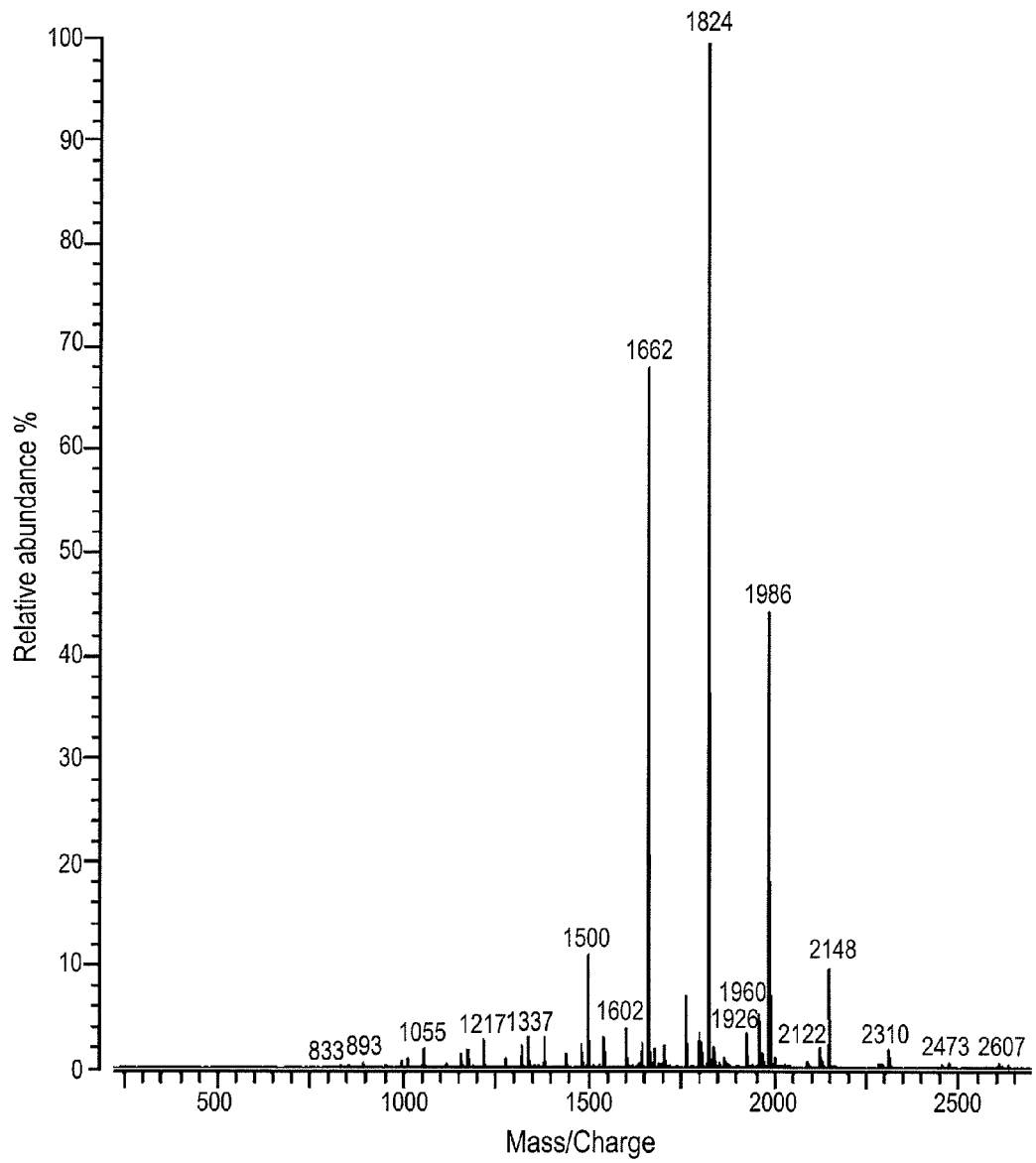
FIG. 2. Positive MALDI-FTICR ion spectrum of GOS-Bio-Gel P-2 fractions. a,b,c,d, and e are fractions (ml) 45, 56, 67, 74, and 82, respectively. Signals with m/z values 527, 689, 851, 1013, 1175, 1337, 1449, 1662, 1824, 1966, 2148, 2310, and 2473 represent sodium coordinated galacto-oligosaccharides with a DP ranging from 3 to 15.
Figure 2B:
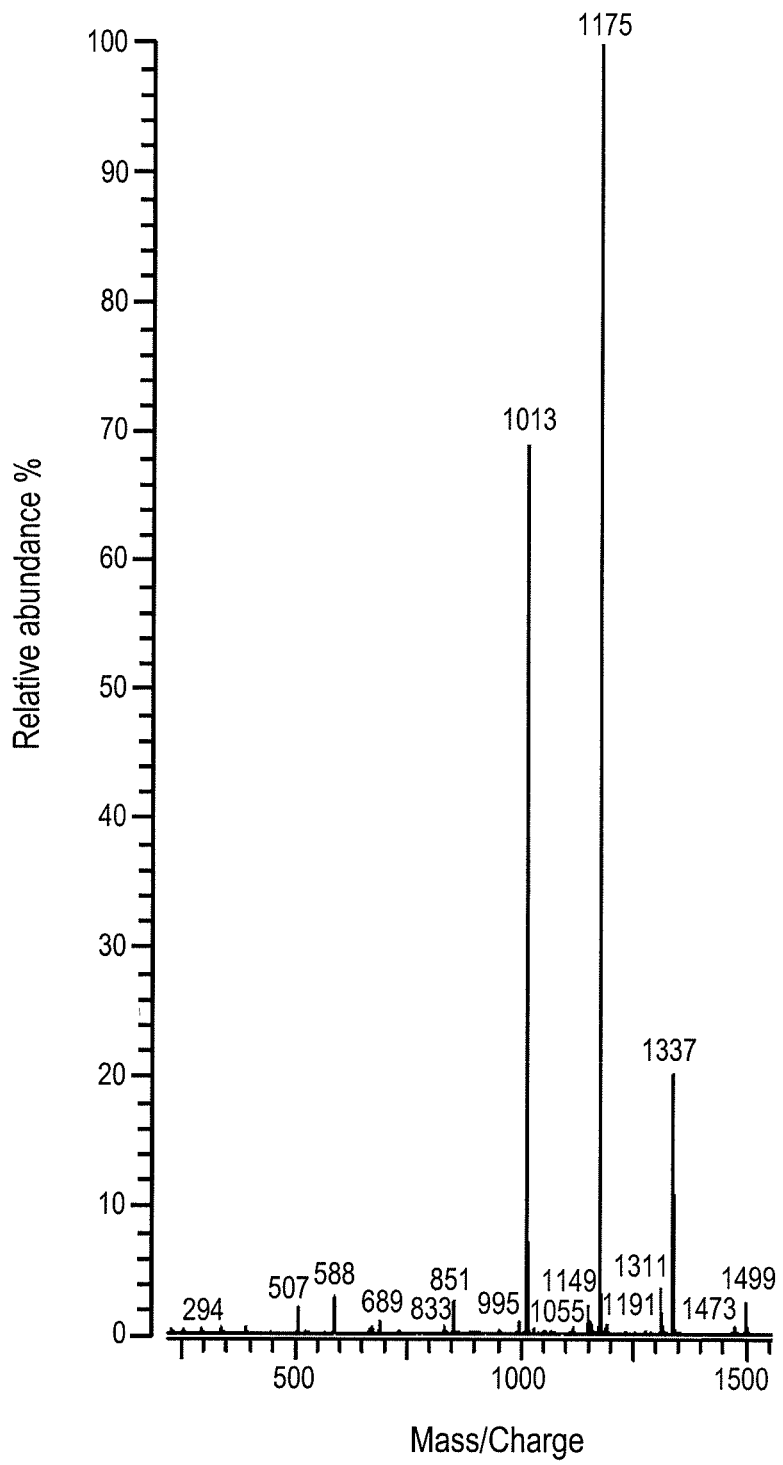
Figure 2C:
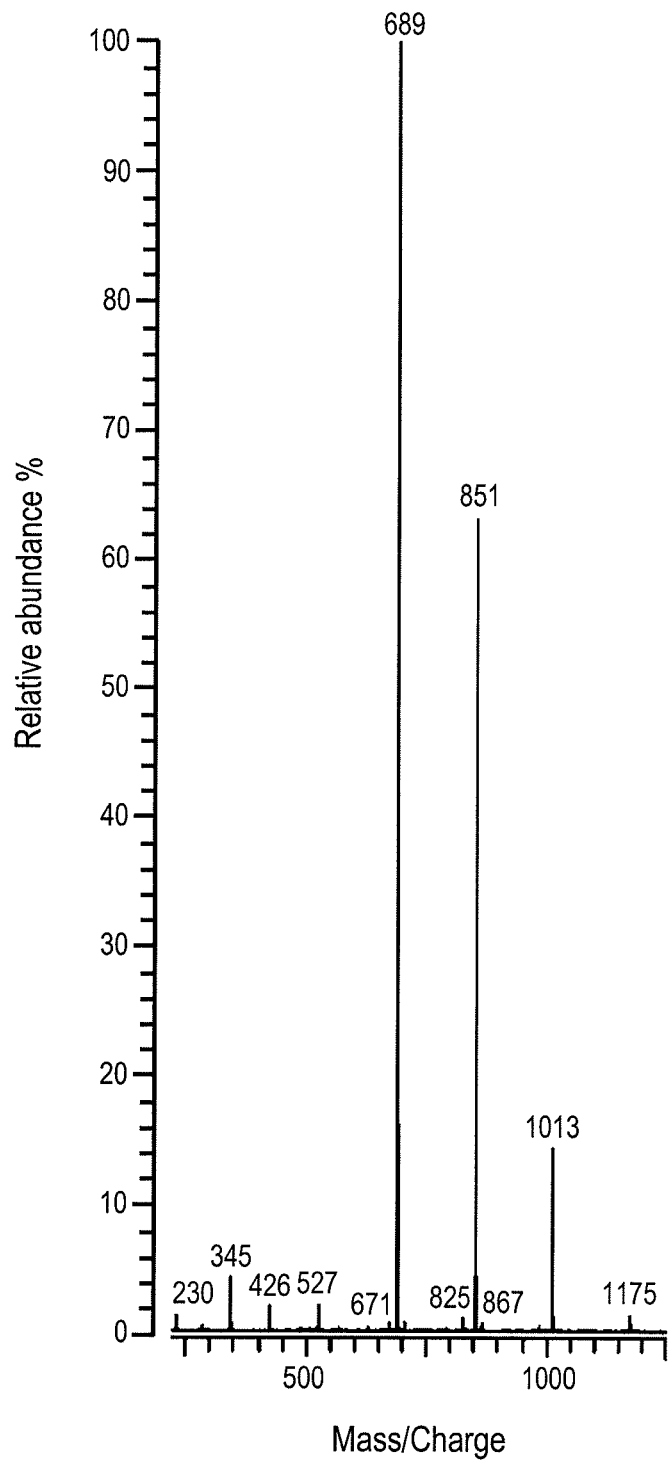
Figure 3A:
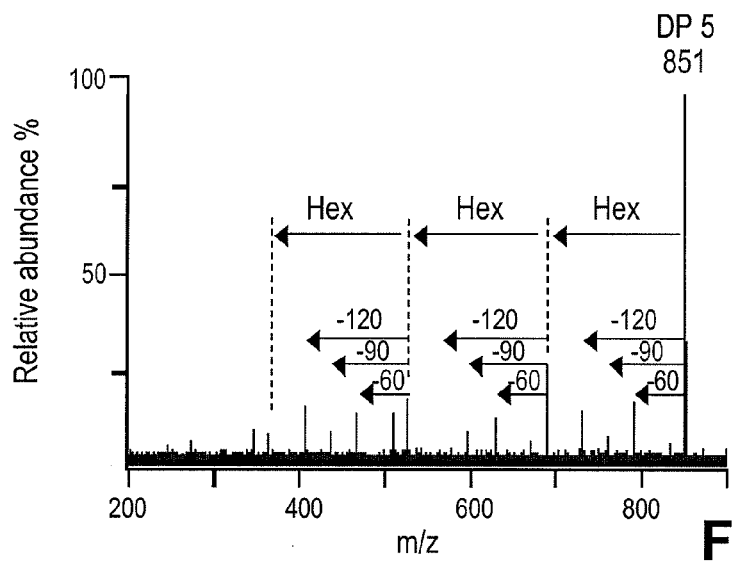
FIG. 3. IRMPD MALDI-FTICR spectra of GOS. A, B and C correspond to galactooligosaccharides with DP 5, 4 and 3, respectively. Fragments ions corresponding to glycosidic-bond cleavages (Hex) and cross-ring cleavages (60, 90 and 120) were obtained.
Figure 3B:
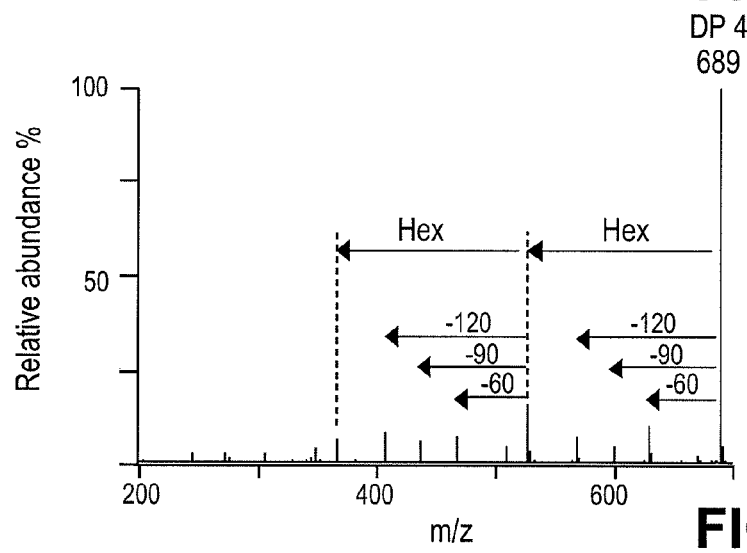
Figure 3C:
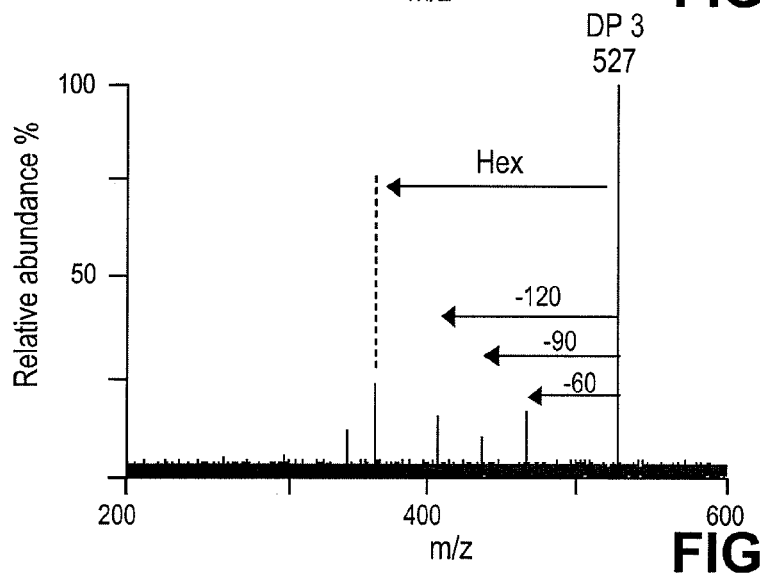

MALDI-FTICR analysis of GOS syrup. To determine the degree of polymerization (DP) of galacto-oligosaccharides in GOS syrup preparations, samples were diluted and analyzed by MALDI-FTICR mass spectrometry. Both glucose and galactose, monomer components of GOS, have an exact residue mass of 162.0528 Da. Exact mass measurement was used to identify the DP of GOS, and the quasimolecular ions were assigned with less than 5 ppm difference between theoretical and calculated mass. Positive ion mode MALDI-FTICR spectrum obtained showed that GOS syrup contains oligosaccharides with DPs ranging from 2 to 11 (FIG. 1). In addition, when GOS syrup preparations where fractionated in a size exclusion chromatography column, MALDI-FTICR analysis of Bio-Gel P-2 excluded fractions showed that GOS mixtures contain oligomers with a DP up to 15 (FIG. 2*a*). Tandem mass spectrometry is usually required to verify composition and elucidate structures; thus, select oligosaccharide ions were interrogated using infrared multiphoton dissociation (IRMPD) tandem MS method. The IRMP mass spectra of GOS with DP 5, 4 and 3 are shown in FIGS. 3 (A, B and C). Fragment ions with shifted masses of 162 toward lower masses were observed, corresponding to glycosidic-bonds cleavages and loss of galactose residues. IRMPD tandem MS analysis also yield fragment ions shifted in 60, 90 and 120 mass units from the parental ion corresponding to cross-ring cleavages fragments.

Figure 4:
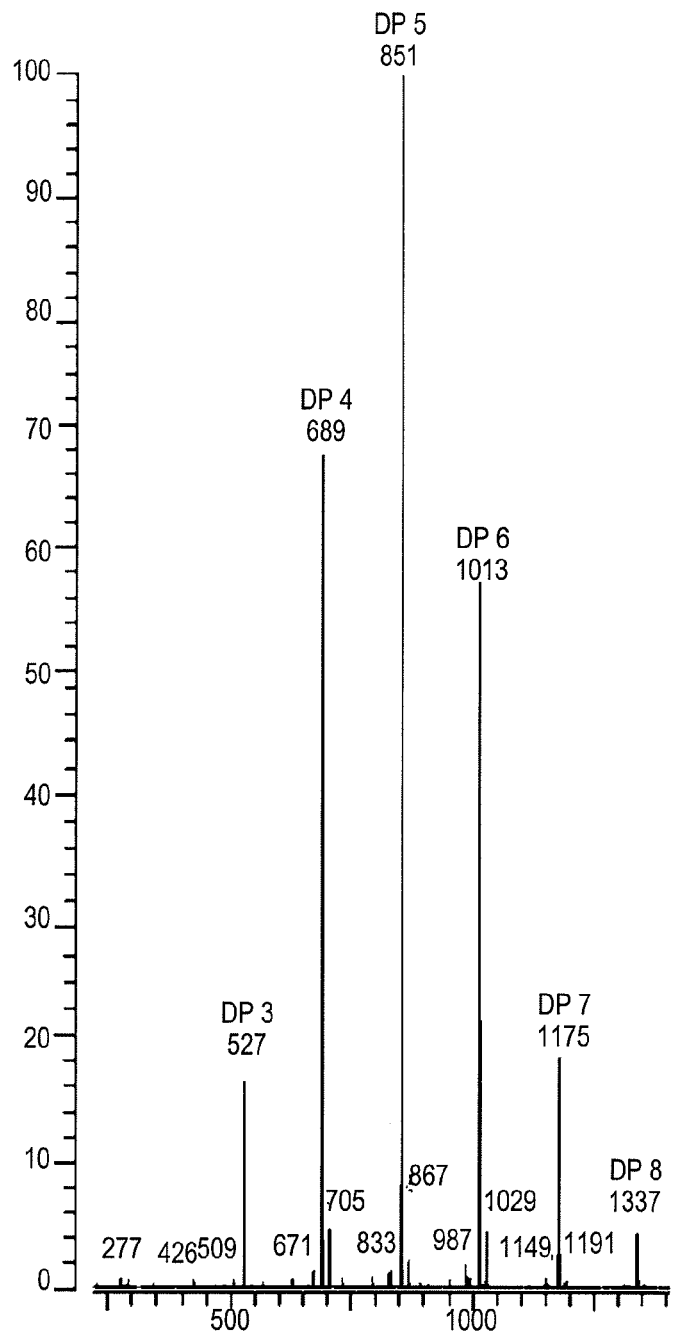
FIG. 4. Positive MALDI-FTICR spectra of pGOS with selected DP used in bifidobacterial fermentation experiments.

GOS purification. To better understand the GUS bifidogenic effect, GOS syrup was fractionated and purified from monosaccharides (glucose and galactose) and disaccharides (including lactose and GOS with DP 2) by size-exclusion chromatography. Fractions were collected and analyzed by MALDI-FTICR, displaying DP of oligomers eluted in each fraction (FIGS. 2a-e). Di- and mono-saccharide-free fractions were confirmed by TLC (data not shown) and pooled according to the desired DP. MALDI-FTICR mass spectrum of purified GOS (pGOS) preparations obtained indicated that the DP ranging from 3 to 8 (FIG. 4).

Rapid-throughput screen of pGOS bifidogenic effect: microscale fermentations coupled to MALDI-FTICR MS analysis. The concept that prebiotics can selectively modulate gastrointestinal microbiota fermentation to influence physiological processes, which are known biomarkers of potential illness and health, has been an important development in nutritional research and food product innovation. However, the lack of analytical methods available to perform comparative analysis of bacterial prebiotics consumption has limited this field. Thus, a fast-throughput method to screen and compare the prebiotic effect of pGOS was developed, coupling bifidobacterial microscale fermentations and pGOS consumption profiling using MALDI-FTICR MS.

pGOS microscale fermentations. Microscale fermentations were performed anaerobically in a 96 well-plate format. The ability to grow on pGOS preparations as the sole carbon source was tested at varying substrate concentrations: 0.5%, 1%, 1.5% and 2%. Four *Bifidobacterium phylotypes* were used in the present work: *Bifidobacterium breve* and *B. longum* subsp. *infantis*, both common infant-associated microbiota, and *B. adolescentis* and *B. longum* subsp. *Longum*, which are typically referred to as "adult-type" *bifidobacteria* (Mitsuoka, T., *Bifid Micro*, 3:11-28 (1984); Ventura, M. et al., *FEMS Microbiol Ecol*, 36:113-121 (2001)).

Growth curves obtained (FIGS. 4A-D) showed that all *bifidobacteria* assayed were able to utilize and grow on pGOS at the four concentrations tested further confirming GOS bifidogenic properties. Interestingly, a differential pGOS growth phenotype was observed among the various assayed *bifidobacteria*. pGOS strongly stimulated the growth of *B. longum* subsp. *infantis*, reaching the highest cell density at all four pGOS concentrations tested ($OD_{600nm}$ 1.2). On the other end, pGOS showed a moderate effect on *B. longum* subsp. *longum* pcultures, producing the lowest endpoint biomass while growing on 0.5% pGOS (max. $OD_{600nm}$ 0.4), with a slight increase in cell mass observed at higher pGOS concentrations (max. $OD_{600nm}$ 0.5-0.7). An intermediate growth profile was displayed by *B. adolescentis* and *B. breve* with a maximum density occurring at $OD_{600}$~0.7 at all pGOS concentrations.

pGOS consumption determined by MALDI-FTICR MS. With the aim to further understand the prebiotic effect of pGOS, a methodology to determine consumption profiles after bifidobacterial fermentation was developed. pGOS remaining in culture supernatants were recovered 72 hours post-inoculation, purified, and analyzed using MALDI-FTICR MS. Positive MALDI-FTICR MS ion spectra of remaining pGOS purified from supernatants of bifidobacterial culture containing 0.5% pGOS are shown in FIGS. 5A-D. A comparative analysis of the mass spectra obtained clearly show a differential fermentative capacity among the *bifidobacteria* assayed, signaling substrate preferences in the utilization of pGOS.

Figure 5A:
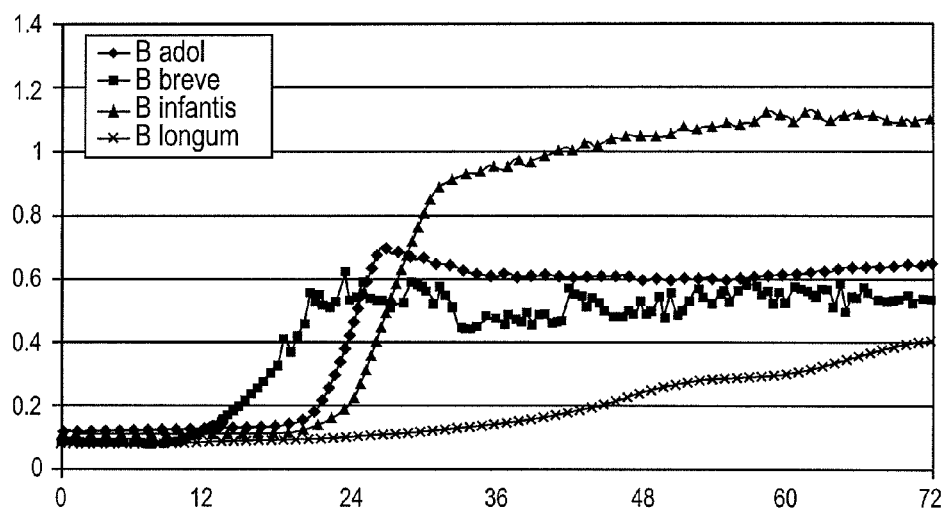
FIG. 5. Growth of *B. adolescentis, B. breve, B. longum* bv. *Infantis*, and *B. longum* bv. *longum* on modified MRS containing: A) 0.5%, B) 1%, C) 1.5% and D) 2% (w:v) of pGOS.
Figure 5B:
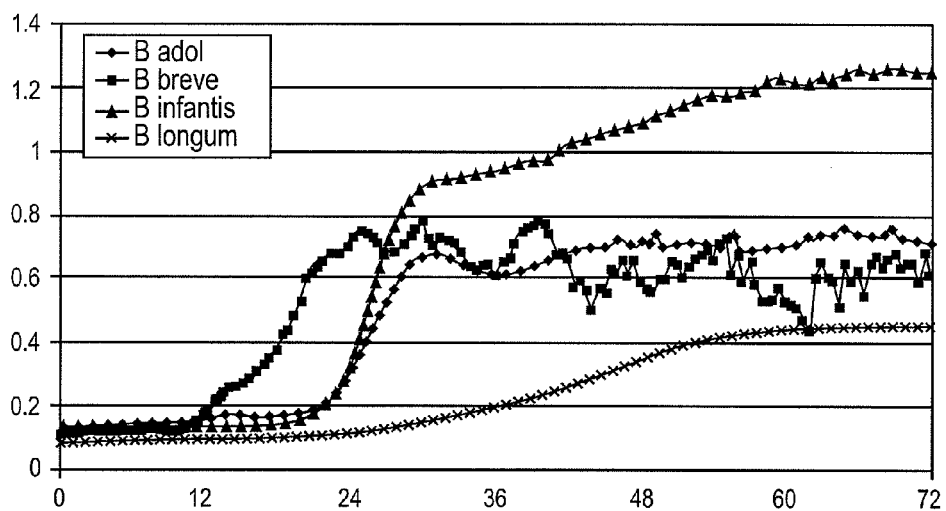
Figure 5C:
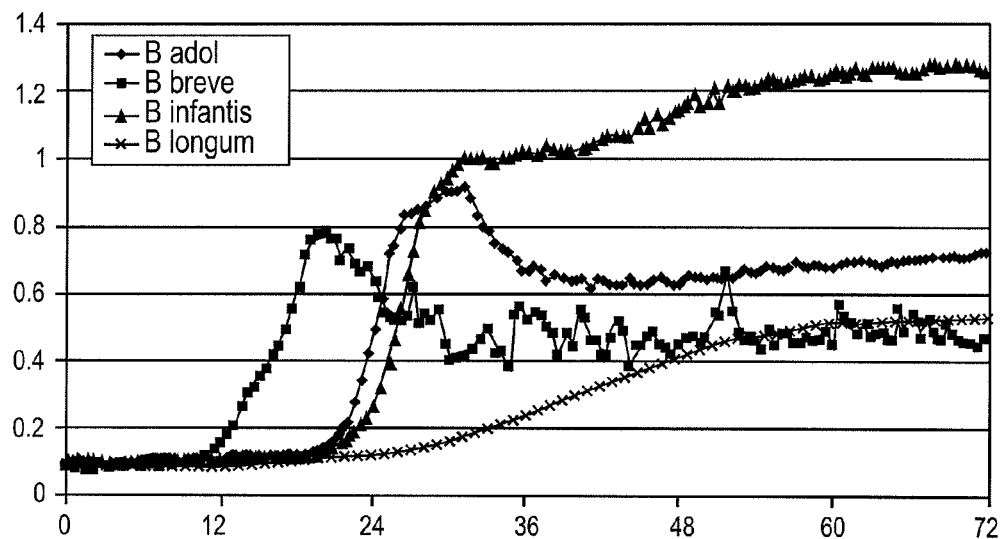
Figure 5D:
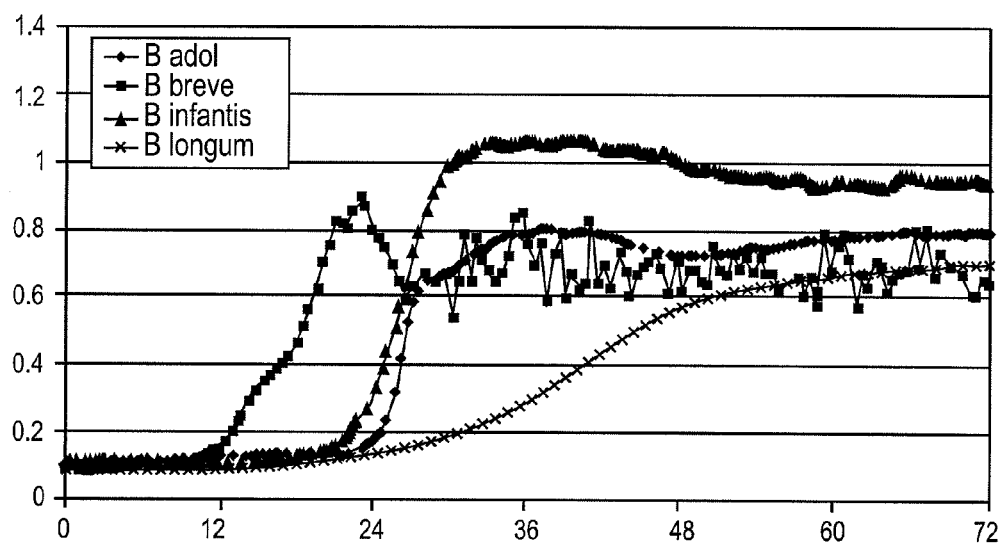

*B. breve* and *B. longum* subsp. *infantis* showed to be the most efficient in pGOS consumption (FIGS. 5b and c). Although slightly different, signals with m/z values 689, 851, 1013, 1175, and 1337 were strongly reduced in both samples, indicating pGOS consumption with DP range from 4 to 8. Remarkably, signal with m/z value 689, corresponding to tetra-saccharides, were almost absent following fermentation by *B. longum* subsp. *infantis*, demonstrating the preferential consumption of pGOS with DP 4. Unlike *B. breve*, *B. longum* subsp. *infantis* also showed an important signal reduction corresponding to oligosaccharides with DP 3. Similarly, *B. adolescentis* showed a significant decrease in signal with m/z value 527, indicating consumption of GOS with DP 3. Although signals corresponding to longer oligosaccharides were not greatly altered, some consumption of oligosaccharides with DP 4 and 5 were evident (FIG. 5a).

Contrastingly, *B. longum* subsp. *longum* did not consume GOS with DP 4 and 5 either, but showed a complete reduction of GOS masses corresponding to DP 6, 7, and 8. Unlike the other strains tested, signals corresponding to trisaccharides were not altered, indicating that pGOS with DP 3 were not consumed by *B. longum* subsp. *longum*.

Genomics of bifidobacterial GOS utilization. The availability of complete genome sequences have enabled various metabolic reconstruction approaches to understand and often predict phenotypes of fermentative bacteria (Schell, M. A. et al., *Proc Natl Acad Sci USA*, 99:14422-7 (2002); Azcarate-Peril, M. et al., *Appl Environ Microbiol*, 74:4610-25 (2008); Sela, D. A. et al., *The Complete Genome Sequence of Bifidobacterium longum subsp. infantis Reveals Adaptations for Milk Utilization within the Infant Microbiome* (Submitted, 2008)).

*Bifidobacteria* have adapted to the utilization of a diverse range of host-indigestible oligosaccharides encountered in the lower bowel. Accordingly, GOS oligomers are degraded to galactose and glucose by bifidobacterial enzymes to generate energy and substrates for anabolic reactions. The requisite catabolic reaction in GOS utilization is β-galactosidase activity (EC 3.2.1.23) exerted on terminal β-galactosyl linkages which are found in industrially produced or naturally occurring GOS. In general, bifidobacterial β-galactosidases are classified into glycosyl hydrolase (GH) family 42 and GH family 2, along with a few exceptions. In addition, several β-galactosidases are fused to other glycosidic domains.

Figure 6:
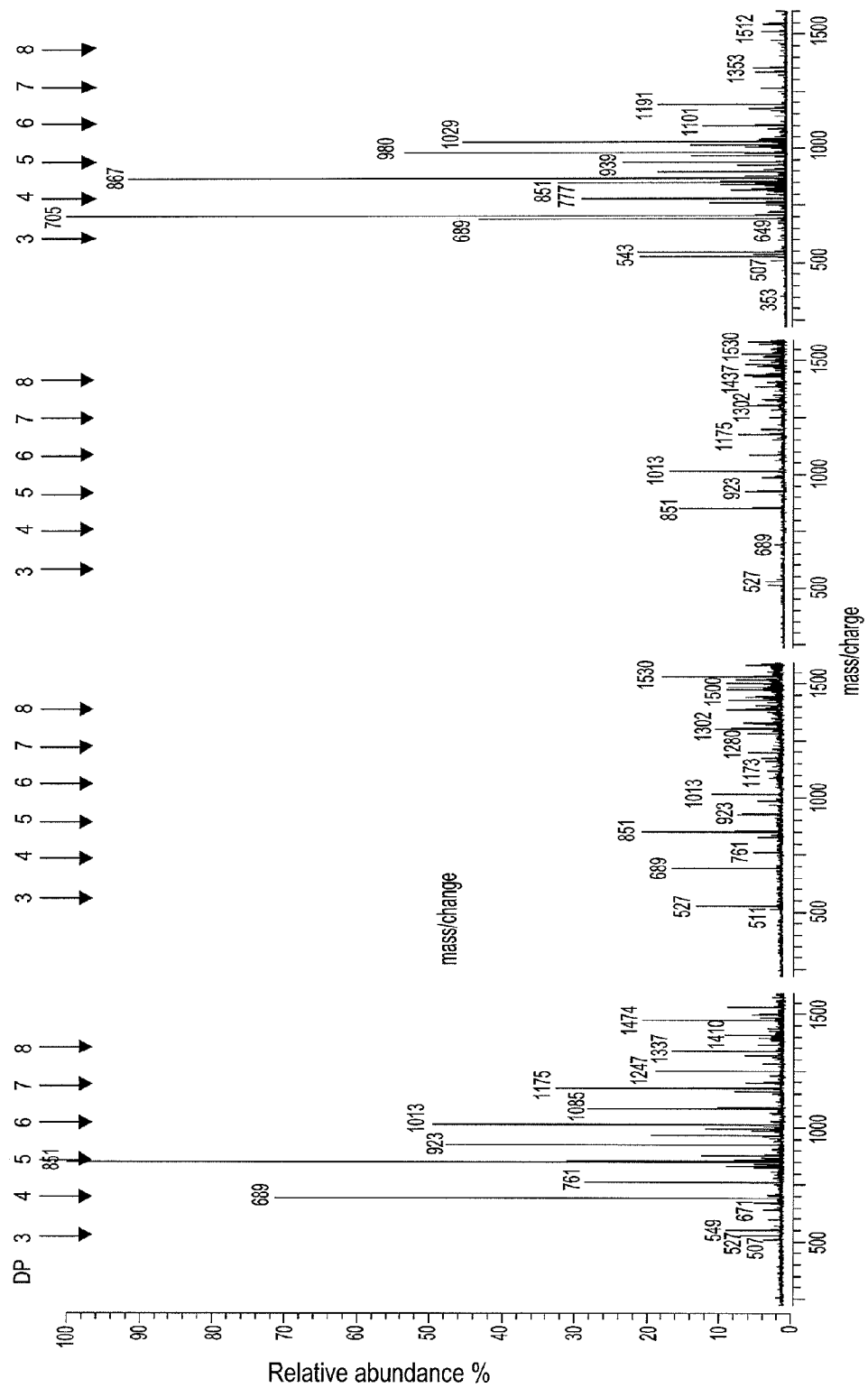
FIG. 6. Positive MALDI-FTICR MS ion spectrum of remaining pGOS purified from supernatants of bifidobacterial culture growth on mMRS containing 0.5% pGOS. A) *Bifidobacterium adolescentis*, B) *B. breve*, C) *B. longum* bv. *Infantis*, and D) *B. longum* bv. *longum*.

Accordingly, the genome sequence of B. adolescentis ATCC 15703, *B. longum* subsp. *infantis* ATCC15697 and *B. longum* subsp. *longum* NCC2705 contains 10, 7, and 3 sequences, respectively, that have been assigned a β-galactosidase functionality (FIG. 6, Table 1). All 20 enzymes are predicted to be intracellular or are secreted by unknown or non-classical pathways as they lack transmembrane helices or signal peptides. Conversely, one *B. bifidum* β-galactosidase isozyme, termed BIF3, possesses a signal peptide and is likely secreted to the extracellular surface, where it is believed to be active in GOS utilization (5). While an exact homolog of BIF3 is not evident in the ATCC15703, NCC2705 or ATCC15697 genomes, a *B. longum* subsp. *infantis* β-galactosidase (Blon__2334; GH 2) with 25% identity is located in a gene cluster dedicated to human milk oligosaccharide (HMO) utilization. Homologs of Blon__2334 are present in two copies: *B. adolescentis* ATCC15703 (BAD__1605 and BAD__1582) and *B. longum* subsp. *longum* NCC2705 (BL__0978) whose genomes do not contain the same complement HMO-related genes found in *B. longum* subsp. *infantis*. Interestingly, these β-galactosidases have been previously isolated and characterized from *B. infantis* HL96 (termed β-gal1) as possessing high transgalactosylation activity (3). The presence of this large β-galactosidase (1023 a.a.) in the *B. longum* subsp. *infantis* HMO cluster, as well as high in vitro transgalactosylation activity, offers a link to oligosaccharide metabolism which may enable *bifidobacteria* to cleave terminal galactosyl residues from GOS and HMO.

operon remains intact along with a duplication of the cluster's β-galactosidase (BAD_01566 and BAD_01567) (FIG. 7). Interestingly, *B. longum* subsp. *infantis* possesses a truncated endogalactanase gene (Blon_0440), which lacks the majority of its catalytic domain and is located next to a degraded β-galactosidase remnant with a complete absence of a proximal sugar transporter (FIG. 7). It appears that these genes became expendable subsequent to the evolutionary diver-

TABLE I

Beta-Galactosidases of the Sequenced Bifidobacteria

| Locus | protein length (aa) | signalP | TM helices | COG | PFAM | GH | notes |
|---|---|---|---|---|---|---|---|
| *B. longum* subsp. *infantis* ATCC15697 | | | | | | | |
| Blon_2334 | 1023 | no | no | COG3250 | 02837, 00703, 00703, 02929 | 2 | unique region, but gene is similar to adol and longum |
| Blon_1905 | 423 | no | no | COG2723 | 00232 | 1 | potential beta-glucosidase |
| Blon_0268 | 606 | no | no | COG3250 | 00703, 02836 | 2 | unique to infantis |
| Blon_0346 | 674 | no | no | COG1874 | 08532 | 42 | unique to infantis, possesses trimerization domain |
| Blon_2016 | 691 | no | no | COG1874 | 02449, 01373, 08532, 08533 | 42/35 | experimental evidence β(1-4) (Hinz, et.al, 2004) |
| Blon_2416 | 706 | no | no | COG1874 | 02449, 08532, | 42/14 | |
| Blon_2123 | 720 | no | no | COG1874 | 02449, 01373, 08532, | 42/5 | experimental evidence β(1-4) (Hinz, et.al, 2004) |
| *B. longum* subsp. *longum* NCC2705 | | | | | | | |
| BL_0259 | 710 | no | no | COG1874 | 02449, 01373, 08532, 08533 | 42 | bgaB |
| BL_0978 | 1023 | no | no | COG3250 | 02837, 00703, 02836, 02929 | 2 | lacZ |
| BL_1168 | 691 | no | no | COG1874 | 02449, 01373, 08532, 08533 | 42/14 | bga |
| *B. longum adolescentis* ATCC15703 | | | | | | | |
| BAD_1605 | 1023 | no | no | COG3250 | 02837, 00703, 02836, 02929 | 2 | lacZ |
| BAD_1582 | 1049 | no | no | COG3250 | 02837, 00703, 02836, 02929 | 2 | lacZ |
| BAD_1534 | 788 | no | no | COG3250 | 02837, 00703, 02836, | 2 | lacZ |
| BAD_0435 | 328 | no | no | COG1874 | 02449, 08532, 08533 | 42 | |
| BAD_1287 | 391 | no | no | COG2723 | 00232 | 1 | potential beta-glucosidase |
| BAD_0156 | 423 | no | no | COG2723 | 00232, 02449 | 1/42 | potential beta-glucosidase |
| BAD_1211 | 688 | no | no | COG1874 | 02449, 08532 | 42 | |
| BAD_1603 | 692 | no | no | COG1874 | 02449, 01373, 08532, 08533 | 42/14 | |
| BAD_1401 | 711 | no | no | COG1874 | 02449, 01373, 08532, | 42/14 | |
| BAD_1402 | 751 | no | no | COG1874 | 01301 | 35 | |

In addition to β-galactosidases, an endogalactanase (EC 3.2.1.89) from *B. longum* subsp. *longum* NCC2705 (BL_0257; GH53) was experimentally determined to release galactotrisaccharides from hydrolysis of β1-4 and β1-3 linkages in GOS. This extracellular enzyme likely acts progressively on GOS molecules with trimeric products imported across the cell membrane. *B. longum* subsp. *longum* preference for GOS with DP≧6 suggests that this endogalactanase is coupled to intracellular transport. The in vitro specificity of purified BL_0257 towards DP≧5 GOS is somewhat consistent with this coupling. The existence of a transporter possessing affinity for galactotrisaccharides to the exclusion of trimeric GOS is strongly supported by the DP3 GOS fraction remaining unaltered following fermentation by *B. longum* subsp. *longum*. Accordingly, the endogalactanase appears in a gene cluster with a potential oligosaccharide transporter (BL_0260-BL_0264), as well as a β-galactosidase (BL_0259) and a lad family regulatory protein (BL_0257) (FIG. 7). The expression of this β-galactosidase and components of the ABC transporter has been recently demonstrated to be upregulated while growing on GOS (Gonzalez, R. et al., *Appl Environ Microbiol*, 74:4686-94 (2008)). This specific response to GOS provides further evidence that this locus is a primary contributor to GOS metabolism in *B. longum* subsp. *longum*. A homolog of this endogalactanase is absent from the *B. adolescentis* genome although the putative GOS gence of subsp. *infantis* and *longum*. This is consistent with the general remodeling of the subsp. *infantis* catabolic potential towards host-derived glycans at the expense of plant sugars such as type I arabinogalactans on which this cluster is active on.

Clearly, the genetics underlying bifidobacterial GOS utilization is diverse and is reflected in their varied consumption glycoprofiles. It is currently unclear if these differential phenotypes are attributable to specific isozymes, unexpected disparity in enzyme localization, variation in signal transduction and regulatory circuits, or other physiological parameters. Likewise, it is possible that specific transporters may facilitate efficient GOS utilization as the ATCC15697 genome encodes twice as many copies of family 1 solute binding proteins (potentially oligosaccharide binding) as the other two fully sequenced *bifidobacteria*.

Discussion

The MALDI-FTICR analysis of GOS clearly demonstrated that oligosaccharides longer than previously described (DP>8) are present in the examined GOS mixtures. These GOS with higher DP did not agree with the manufacturer's claim and is likely due to the superior sensitivity of FT-ICR mass spectrometry over HPLC and NMR techniques previously used for GOS analysis (Dumortier, V. et al., *Carbohydr Res*, 201:115-23 (1990); Kimura, K. et al., *Carbohydr Res*, 270:33-42 (1995); Van Laere, K. M. et al., *Appl Environ*

Microbiol, 66:1379-84 (2000)). In general, the efficacy of prebiotics toward promoting human health has been strongly related to their chemical structure (Casci, T. et al., *In Functional food and Biotechnology*, pp. 401-434, Ed Taylor and Francis (2007)). It is known that GOS structures are highly variable and dependent on the enzyme and conditions used during their synthesis process; thus oligosaccharides with the same DP can contain up to eight isomeric structures (Dumortier, V. et al., *Carbohydr Res*, 201:115-23 (1990); Kimura, K. et al., *Carbohydr Res*, 270:33-42 (1995); Yanahira, S. et al., *Biosci Biotechnol Biochem*, 59:1021-6 (1995)). (TANDEM) Select oligosaccharide ions were interrogated using infrared multiphoton dissociation (IRMPD) tandem MS method.

All together, these variations observed in bacterial growth reflect that pGOS selectively stimulates the development of specific bifidobacterial phylotypes in a differential manner. Collectively, MALDI-FTICR mass spectrometry analysis of remaining sugars after fermentation experiments accurately demonstrated species-specific bifidobacterial preferences on pGOS utilization with certain DP. Two predominant species encountered in the infant GIT, *B. breve* and *B. longum* subsp. *infantis*, were more effective in utilizing a diverse range of pGOS masses hinting at a potential adaptive advantage within the infant intestinal environment, where human milk has provided GOS over evolutionary time.

Previous studies on carbohydrate utilization by *bifidobacteria* have found that individual strains possess specific substrate preferences towards monosaccharide mixtures containing glucose, mannose, galactose, arabinose, and xylose (Macfarlane, G. T. et al., *Journal of Applied Microbiology*, 104:305-44 (2008)). In addition, preferences for different prebiotic substrates, including galacto-oligosaccharides, have been largely described in comparative growth and/or fecal enrichment approaches (Sako, T. et al., *Int Dairy J*, 9:69-80 (1999); Rabiu, B. A. et al., *Appl Environ Microbiol*, 67:2526-30 (2001); Perez-Conesa, D. et al., *Journal of Food Science*, 70:6, M279-85 (2005); Perez-Conesa, D. et al., *Journal of Food Science*, 71:1, M7-11 (2006); Vernazza, C. L. et al., *J Appl Microbiol*, 100:846-53 (2006); Depeint, F. et al., *Am J Clin Nutr*, 87:785-91 (2008)). So far, GOS consumption with specific DP has only been determined in *B. adolescentis* cultures using HPAEC-PAD (Van Laere, K. M. et al., *Appl Environ Microbiol*, 66:1379-84 (2000)). However, the relative concentration of oligomers could not be accurately determined due to the significant variation of the response factor of the detector (PAD) toward oligosaccharides with higher DP.

Conclusions

This work demonstrates, for the first time, the genuine bifidogenic effect of purified galacto-oligosaccharides with DP from 3 to 8, in pure in vitro cultures of the major bifidobacterial species present in the infant and adult GIT. Our results demonstrate that pGOS selectively stimulates the different bifidobacterial phylotypes.

In addition, a high-throughput analytical method was developed to compare pGOS consumption after *Bifidobacteria* fermentation. Selectivity was also demonstrated, highlighting pGOS' potential for the rational design and development of functional food, which can target the enrichment of select bifidobacterial phylotypes.

Our results show that MALDI-FTICR is a useful tool for comprehensive profiling of oligosaccharide species within GOS mixtures and enhances the speed to rapidly investigate the prebiotic effect of GOS, can be easily applied to other oligosaccharides, non-digestible carbohydrates or any other polymeric system.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for stimulating beneficial *Bifidobacterium* microflora in an animal, the method comprising
    administering to the animal a sufficient amount of a prebiotic composition to stimulate colonization of the gut of the animal by a strain of *Bifidobacterium breve* or *Bifidobacterium longum* bv. *infantis*,
    wherein the prebiotic composition comprises galacto-oligosaccharides and substantially lacks fructo-oligosaccharides, and
    wherein at least 50% of the galacto-oligosaccharides by weight are tetra or penta galacto-oligosaccharides or
    wherein at least 30% of the galacto-oligosaccharides by weight are tetra galacto-oligosaccharides,
    thereby stimulating colonization of the gut of the animal by the strain of *Bifidobacterium breve* or *Bifidobacterium longum* bv. *infantis*.

2. The method of claim 1, wherein the animal is a human.

3. The method of claim 1, wherein the animal is a non-human mammal.

4. The method of claim 2, wherein the human is less than 5 years old.

5. The method of claim 2, wherein the human is over 50 years old.

6. The method of claim 2, wherein the human has a condition selected from the group consisting of inflammatory bowel syndrome, constipation, diarrhea, colitis, Crohn's disease, colon cancer, functional bowel disorder, irritable bowel syndrome, and excess sulfate reducing bacteria.

7. The method of claim 1, wherein the composition has less than 20% by weight of dimeric galacto-oligosaccharides, based on weight of the total oligosaccharides.

8. The method of claim 1, wherein the composition has less than 10% by weight of dimeric galacto-oligosaccharides, based on weight of the total oligosaccharides.

9. The method of claim 1, wherein the composition has less than 5% by weight of monomeric sugars based on total sugar and oligosaccharide solids.

10. The method of claim 1, wherein the composition has less than 5% by weight of lactose, based on weight of the total oligosaccharides.

11. The method of claim 1, wherein less than 10% of the galacto-oligosaccharides by weight have a degree of polymerization of 6 or greater.

12. The method of claim 1, wherein the composition has greater than 50% tetra galacto-oligosaccharides.

13. The method of claim 1, wherein the composition has greater than 60% tetra galacto-oligosaccharides.

14. The method of claim 1, wherein the composition has greater than 30% penta galacto-oligosaccharides.

15. The method of claim 1, wherein the strain is a strain of *Bifidobacterium longum* bv. *infantis*.

16. The method of claim 1, wherein the composition has less than 10% by weight of trimeric galacto-oligosaccharides, based on weight of the total oligosaccharides.

17. The method of claim 1, further comprising administering to the animal a strain of *Bifidobacterium breve* or *Bifidobacterium longum* bv. *infantis*.

18. The method of claim 17, wherein the strain is a strain of *Bifidobacterium breve*.

19. The method of claim 17, wherein the strain is a strain of *Bifidobacterium longum* bv. *infantis*.

* * * * *